(12) United States Patent
Neev

(10) Patent No.: US 9,067,060 B2
(45) Date of Patent: Jun. 30, 2015

(54) SKIN TREATMENT AND HAIR TREATMENT DEVICE WITH PROTRUDING GUARDS

(76) Inventor: Joseph Neev, Laguna Beach, CA (US)

( * ) Notice: Subject to any disclaimer, the term of this patent is extended or adjusted under 35 U.S.C. 154(b) by 1587 days.

(21) Appl. No.: 11/738,392

(22) Filed: Apr. 20, 2007

(65) Prior Publication Data

US 2007/0255359 A1 Nov. 1, 2007

Related U.S. Application Data

(60) Provisional application No. 60/793,992, filed on Apr. 20, 2006.

(51) Int. Cl.
*A61N 5/06* (2006.01)
*A61B 18/20* (2006.01)
*A61B 18/00* (2006.01)
*A61B 19/00* (2006.01)
*A61N 5/00* (2006.01)

(52) U.S. Cl.
CPC ............ *A61N 5/0613* (2013.01); *A61B 18/203* (2013.01); *A61B 2018/00005* (2013.01); *A61B 2018/00017* (2013.01); *A61B 2018/00023* (2013.01); *A61B 2018/00452* (2013.01); *A61B 2018/00458* (2013.01); *A61B 2018/0047* (2013.01); *A61B 2018/00476* (2013.01); *A61B 2019/306* (2013.01); *A61B 2019/465* (2013.01); *A61N 5/0616* (2013.01); *A61N 5/0617* (2013.01); *A61N 2005/007* (2013.01)

(58) Field of Classification Search
CPC .................. A61B 18/203; A61B 2018/00636; A61B 2019/465; A61N 5/0616; A61N 5/0617; A61N 2005/007
USPC .......................... 128/898; 606/9; 607/88–94
See application file for complete search history.

(56) References Cited

U.S. PATENT DOCUMENTS

| | | | | |
|---|---|---|---|---|
| 5,125,923 A * | 6/1992 | Tanner et al. | | 606/10 |
| 5,947,957 A * | 9/1999 | Morris | | 606/13 |
| 5,968,033 A * | 10/1999 | Fuller et al. | | 606/9 |
| 6,261,310 B1 * | 7/2001 | Neuberger et al. | | 607/89 |
| 6,730,113 B2 * | 5/2004 | Eckhardt et al. | | 607/94 |
| 6,761,730 B1 * | 7/2004 | Johnson et al. | | 607/94 |
| 6,790,205 B1 * | 9/2004 | Yamazaki et al. | | 606/9 |
| 2002/0002391 A1 * | 1/2002 | Gerdes | | 607/89 |
| 2002/0120256 A1 * | 8/2002 | Furuno et al. | | 606/9 |
| 2004/0030325 A1 | 2/2004 | Cahir et al. | | 606/9 |
| 2004/0176754 A1 * | 9/2004 | Island et al. | | 606/9 |
| 2010/0145321 A1 * | 6/2010 | Altshuler et al. | | 606/9 |

* cited by examiner

*Primary Examiner* — Gary Jackson
*Assistant Examiner* — Scott T. Luan
(74) *Attorney, Agent, or Firm* — Richard B. Cates

(57) ABSTRACT

The present invention relates to the fields of skin care and energy-tissue interaction. More particularly, the invention relates to a device and method for enhancing operation and treatment safety during applications of energy to the skin and human body.

17 Claims, 24 Drawing Sheets

1.) Protruding guards as coolers with through light

1.) Protruding guards

1.) Protruding guards for HAIR, FOR ACNE

1.) Protruding guards as coolers with through light

Top view of the
Supporting frame

Top view of the Thin film
Opto-thermal absorbing film
To be glued to the top of the
frame.

1612 Alternative
support frame for the
OTC film – more
drills

1612 Alternative support frame for the OTC film – more drills

SKIN TREATMENT AND HAIR TREATMENT DEVICE WITH PROTRUDING GUARDS This application claims priority to U.S. provisional application Ser. No. 60/793,992 filed Apr. 20, 2006 which is hereby incorporated by reference in its entirety.

FIELD OF THE INVENTION

The present invention relates to the fields of skin care.

BACKGROUND

Many methods in dermatology, plastic and cosmetic surgery, as well as cosmetic and over the counter home treatments of skin ailment and skin conditions include application of energy and in particular application of light energy or laser energy. Applications such as treatment of acne, pigmented lesions, vascular lesions, removal of hair or enhancement of hair growth, as well as exfoliations and treatment of scar tissue, require the application of a variety of energy or power levels from such light or laser source. An obvious problem of safety arises with regards to the exposure of eyes, injured skin locations, or other sensitive tissue that may be damaged or endangered in the course of such treatments. The problem become particularly important in view of the growing popularity of such light and laser based devices in home use by consumers and the non-professional public. Over the counter use or use by patients in Over-the-counter physician prescribed use is also growing in popularity. The popularity of electric and electronic based home-use acne treatment, skin rejuvenation, microdermabrasion and hair treatment devices is also rapidly growing. At present there are no such safety features on the consumer market. Interlocks are available for doors to operating rooms in the hospitals. Such interlocks prevent entry of unauthorized personal to the operating room, for example, when a surgical laser unit operates.

There is therefore an immediate, urgent, and growing need for safety features that will prevent the users of such technology, whether at home by consumers or by professional users such as doctors, nurses, dentists, hygienists and physician assistants, for devices that will prevent accidents, accidental exposures, and misuse of such technologies.

SUMMARY OF THE INVENTION

The present invention comprises a device that can be operatively coupled to any existing or contemplated medical or home use treatment device to prevent exposure of eyes or other sensitive skin or tissue to dangerous exposures of energy. The device comprise a member that extends at least partially into the path of the emitted treatment energy and prevents the emission of such energy unless the area about to be exposed to said emitted energy exert a physical force on said member. Said physical force must be strong enough to cause discomfort to injury-prone locations such as, for example, eye, injured skin, injured tissue, or pain-sensitive parts of the body.

Additionally and preferably, the present invention comprises systems, devices and methods in which a device has an emitter that emits a first energy along a path, a member that extends at least partially into the path and a circuit couples activity of the emitter with movement of the first member.

In an alternative preferred embodiment of the present invention, the present invention comprises systems, devices and methods in which a device has an emitter that emits a first energy along a path, a member that extends at least partially into the path and a mechanical coupler that couples activity of the emitter with movement of the first member.

All suitable emitters are contemplated, including coherent and incoherent energy sources, visible and non-visible wavelengths, and those that emit electromagnetic and/or other energy. Of particular interest are flashlamps, because they are inexpensive, and their energy is difficult to focus to a spot size that is likely to lead to retinal injury.

Emitters are preferred that have energy density of less than 30 J/cm$^2$, more preferably less than 20 J/cm$^2$, more preferably less than 10 J/cm$^2$, more preferably yet less than about 3 J/cm$^2$ and most preferably less than 1.5 J/cm$^2$. On the other hand, devices are contemplated that will be used for treatment of skin, and especially devices that can emit energies sufficient to cause damage to a retina of an eye. This includes, for example, laser hair removal treatment, laser skin rejuvenation, laser removal of tattoos, light treatment for acne, light treatment for hair reduction, laser or light treatment for removal of vascular lesions, and heat treatment for acne.

The member can have any desired size or shape, provided that the member can still serve as a interrupter not allowing the device to emit energy unless the member has been modified by the location targeted for treatment in a way that would cause discomfort to injury-prone locations such as, for example, eye, injured skin, injured tissue, or pain-sensitive parts of the body. For robustness, the member preferably has a length of no greater than 3, 4, 5, 6, 7, 8, 9, or 10 mm, depending in part upon the type of material, cross-section. There can be multiple members, which can operate independently from one another, or mechanically coupled in some way, for example by being coupled to a common foot. For example, the entire treatment window through which the energy pass to the target can serve as a member where the window, for example, has to be mechanically disturbed or pressed before energy can be emitted. Alternatively multiple independent members can operate independently. This mode of operation is useful in making it difficult for an inexperienced user (for example a child) to press all multiple members at the same time. If the device is designed so that energy is emitted only if all members position has to be modified simultaneously (for example, all members has to pushed in by at least 2 mm) then only a flat surface such as a target surface appropriate for treatment can cause such activation. The eye would be too sensitive to the touch. A child trying to push the multiple members with his fingers would find it difficult to coordinate such a multiple push without also at least partially blocking the beam.

The circuit preferably precludes the emitter from emitting the energy unless the first member is depressed. The amount of depression can be less then 5 mm and preferably less than 3.5 mm and most preferably less than 2 mm. An aiming beam is also contemplated, preferably one having a lower energy density, and/or a different wavelength from the main emitted energy. Said aiming beam can be on when the device is turn on and operate independently of the member that control the activation of the main beam because the aiming beam energy is substantially less powerful than the treatment energy that is designed to operate at power level sufficient for surgical or therapeutic purposes or at power levels designed to achieve tissue modifications or cosmetic improvements.

The invention also contemplates a second member so that the device control circuit also couples activity of the emitter with movement of a second member. The characteristics of the second member can be similar to that of the first member described above.

The invention also contemplates the possibility of the first and second members are coupled to a common foot. If both members are coupled to the common foot a better stability of operation may be obtained.

13. The device of claim 1, wherein the first member includes an expanded portion that absorbs at least 30% of the first energy.

The invention also contemplates the device discussed above with the first member being cooled to protect the surface of the treatment target, for example the surface of the skin. If the surface of the skin is subject to high treatment energy, the first member may be cooled so that when it is in contact with the skin it keep it cooled. For example, the surface of the skin may be cooled below 10° C., and preferably below 5° C. and most preferably below 3° C. In this embodiment the cooling element can be any cooled component capable of serving as a first member as described above but also cooled to so that upon contact with the skin it will absorb some of the skin temperature. For example, said first member can be passively cooled in a refrigerator or a freezer and brought to the desired temperature so it can bring the surface of the skin down to the temperatures described above. Alternatively and preferably, said first member can also be actively cooled.

The invention also contemplates using the first member of the device discussed above to incorporate an active cooling element capable of cooling the skin upon contact. In this embodiment, the cooling element can, for example, be made of similar material to those used in thermoelectric coolers (TEC) and incorporated into the first member. The cooling element can, for example, be made of TEC so it also serves the function of the first member as described above. The cooling element can further comprise active cooling element that actively cools the first member for example, a circulating coolant such as Freon-like gases can be used to circulate inside said member to actively cool first member.

The invention further contemplates incorporating the member of the device as a cooling element that has sufficient cooling capacity such that when the energy is applied at an energy density of at least 15 J/cm2 to a skin having an epidermal-dermal junction, the junction remains below 50° C. The invention further contemplates that that when the energy is applied at an energy density of at least 10 J/cm2, and more preferably at an energy density of at least 5 J/cm2 and most preferably at an energy density of at least 1.5 J/cm2 to a skin having an epidermal-dermal junction, the junction remains below 50° C.

The invention further contemplate that the cooling element is activated at a predetermined time subsequent to a detected movement of the first member. The amount of movement and required force on the member should be similar or greater to that required to activate the energy source. Thus, preferably, an activation of the energy source, also activates the cooling element. Most preferably, the movement of the first member as described above, should activate the cooling element prior to the activation of the energy source and the emission of energy. For example, the activation of the cooling element subsequent to the detection of movement of the first member should precede the activation of the energy source by about 1 second, and more preferably by about 0.2 seconds and more preferably yet by about 0.1 second and most preferably by about 0.05 second.

The invention further contemplates that the first member includes a fluid path through which a fluid is dispensed. For example, the foot of the first member can be hollow and contain, for example, a therapeutic fluid such as benzyl peroxide for the treatment of acne. Alternatively and also preferably, the fluid may be, for example, antibiotic for reduction of bacteria, or ALA compound to be followed up by a light dosage for a Photodynamic therapy (PDT) treatment. Most preferably the fluid can, for example, contain vitamin and minerals, or nutrient to nourish the skin or hydrate the skin. The fluid path within the member can be designed, for example, to include a series of perforation at the foot of said first member, said perforations are blocked by, for example, a membrane or a thin film that can be actively coupled to the device circuit so that the membrane or thin film are removed and allow flow of the fluid through the perforations and onto the skin surface upon detection of the movement of the first membrane.

Preferably the invention also contemplate that the first membrane that include a fluid path through which fluid can be dispensed includes a foot, wherein the surface of the foot of the first membrane is rough or contain shaper edges, for example edges that protrude beyond said foot surface from about 0.01 mm to 0.6 mm. Such a design will allow the foot to remove some of the skin upper layers as it contacts and moved across the skin surface, thus enhancing the delivery of the fluid contained within the first member or within the device across the surface of the skin and into the skin.

In a preferred embodiment the invention further contemplates that the first member includes a resistive heating element that allow heating of the surface of the skin. The resistive heating element may include a resistor capable of heating the surface of the skin to less than about 400 degrees centigrade, and preferably to less than about 300 degrees centigrade and more 200 degree centigrade, and more preferably yet to 150 degrees centigrade and most preferably to less than about 75 degrees centigrade. Preferably, the resistive heating element within the first member heat surface for a time duration of about 3 minutes, more preferably to a time duration of about 2 minutes, more preferably yet for a time duration of about 1 minutes, alternatively and also preferably for a time duration of about 1 minute or less, more preferably yet to a time duration of about 200 ms, and most preferably to a time duration of about 20 ms or less.

Preferably, the resistive heating element within the first member also include an insulating layer distal to the heating element. Said insulating layer may be composed of Teflon or polycarbonate or other suitable insulating element. Alternatively and preferably said insulating layer may also be transparent to the device energy, for example, made of polycarbonate, glass, or clear plastic. Alternatively and preferably, the insulating layer may be transparent to the device energy, electrically insulating but allow some heat conduction for example, made of sapphire.

From a method perspective the invention contemplate a method for treatment of skin ailment wherein energy is applied to a targeted surface but said energy is allowed to interact with the surface only if a step of disturbing a member actively coupled to the circuit that trigger the emission of the energy, takes place first. In this preferred embodiment takes the following steps: Aiming the energy generating source at the target area. Bring the energy generating source to the vicinity of the target area, allow a first member probe to interact with the target area, the interaction step then generate a feedback signal to the energy source that at a pretty determine level, for example, if the first member experience a force sufficient to, upon contact, cause discomfort to a human eye or injured area of the target skin, allow the final step of energy emission direct to the target area on the skin to take place.

In yet another preferred embodiment, the device the first member also prevents the device from contacting the targeted material. Alternatively and preferably said first member prevents the device from coming into a direct contact with the skin. This is important to avoid overheating of the skin if the window or lens allowing the energy to emerge from the device and into the targeted skin tissue become over heated as it is used to treat the skin ailment. Thus even without being cooled, possible heated device transfer of thermal energy is minimized due to first member preventing the device from coming into a direct contact with the skin.

The present invention also comprise a device that can be operatively coupled to any existing or contemplated medical or home use treatment device to prevent exposure of eyes or other sensitive skin or tissue to any form of dangerous or unsafe mechanical energy, for example, first member can be inserted in the mechanical energy carrier path, for example a needle, vacuum suction, dermabrasion, microdermabrasion, or a blunt mechanical energy carrier, to prevent activation of said mechanical energy carrier unless first member is moved to a predetermined level. Thus first member may for example, be actively coupled to mechanical energy carrier so it is not activated unless the first member is depressed by less then 5 mm with a force that is sufficient to cause discomfort to the eye or injured tissue. Alternatively and preferably, said first member may have to be pressed by less than 2 mm and most preferably less than 1 mm.

In yet further elaboration of this preferred embodiment, first member may be coupled to a foot. The foot is designed to contact the targeted skin. When the device is pressed again the targeted skin as described above, the emitted energy or mechanical energy carrier (for example a needle) is activated and pass through an opening in the foot to impact the skin. The pressure of said first member and the foot it is couple too is sufficient to reduce the amount of pain caused by said energy or mechanical energy carrier (for example a needle) as it impact the skin or target tissue. For example, the pressure the first member and the foot it is couple to preferably exert a pressure on the skin that is sufficient from stopping blood flow to the skin in order for said energy source to be activated.

In a further preferred embodiment of the present invention the circuit precluded the emitter from emitting the energy unless the first member is depressed by a force sufficient to reduce blood circulation in the skin above the mid-reticular dermis.

In an additional preferred embodiment of the present invention, the device include an energy carrier for example a needle and the circuit in the device preclude the needle from moving toward the skin unless first member is depressed by a force sufficient to reduce blood circulation in the skin above the mid-reticular dermis.

In an alternative preferred embodiment of the present invention, the present invention comprises systems, devices and methods in which a device has an emitter that emits a first energy along a path, a member that extends at least partially into the path and a mechanical coupler that couples activity of the emitter with movement of the first member In a preferred embodiment the circuit or mechanical coupler precluded the emitter from emitting the energy unless the first member is depressed by a force sufficient to reduce the sensation of pain.

In other aspects, devices and methods are contemplated for treating tissue with energy, comprising: directing the output of an energy emitter towards a tissue; extending a first member at least partially into the path the energy would follow between the energy source output and the target; and coupling the activity of the energy with the movement of the first member. In preferred embodiments the first member includes a resistive heating element, which can advantageously include an insulating layer distal to the heating element. It is contemplated that the first member prevents can contact both any part of the device and the target surface, while at the same time preventing the housing of the device from contacting the tissue. Mechanical and al other suitable energies are contemplated. All suitable emitters are contemplated, including for example a diode or a flash lamp, and can be physically disposed in a larger or smaller area (e.g. a needle).

In other aspects, devices and methods are contemplated for treating tissue the method that comprise: directing the output of an energy emitter towards a tissue; extending a first member at least partially into the path the energy would follow between the energy source output and the tissue; coupling the activity of the energy with the movement of the first member. In preferred embodiments the a first member can extend at least partially into the path, and contemplated devices and method can further comprise a circuit that couples activity of the emitter with movement of the first member.

In yet other aspects, devices and methods are contemplated for modifying tissue and reducing body fat, comprising: an energy source; a conduit to deliver the energy to a target tissue; and activating the energy until it reduces the fat to a form that can be readily removed. In preferred embodiments the energy source emits emitting electromagnetic energy and the conduits consisting of an optical fiber. Also in preferred embodiments the electromagnetic energy is at least partially absorbed by an absorbance enhancing substance, and the absorption enhancing substance is dispensed at the distal end of said fiber. Additionally, it is contemplated to include a sensor capable of monitoring the extent of the absorbing enhancing substance extending within the targeted fat or other tissue.

BRIEF DESCRIPTION OF THE DRAWING

The accompanying drawings, which are incorporated herein and form part of this invention description, illustrate embodiments of the invention and together with the description, serve to explain the principles of the invention.

FIG. 1A. illustrates how pores on the human skin are opened in response to application of thermal energy.

DETAILED DESCRIPTION

Other objects and advantages of the present invention will become apparent from the following description and accompanying drawings.

Figure 1A:
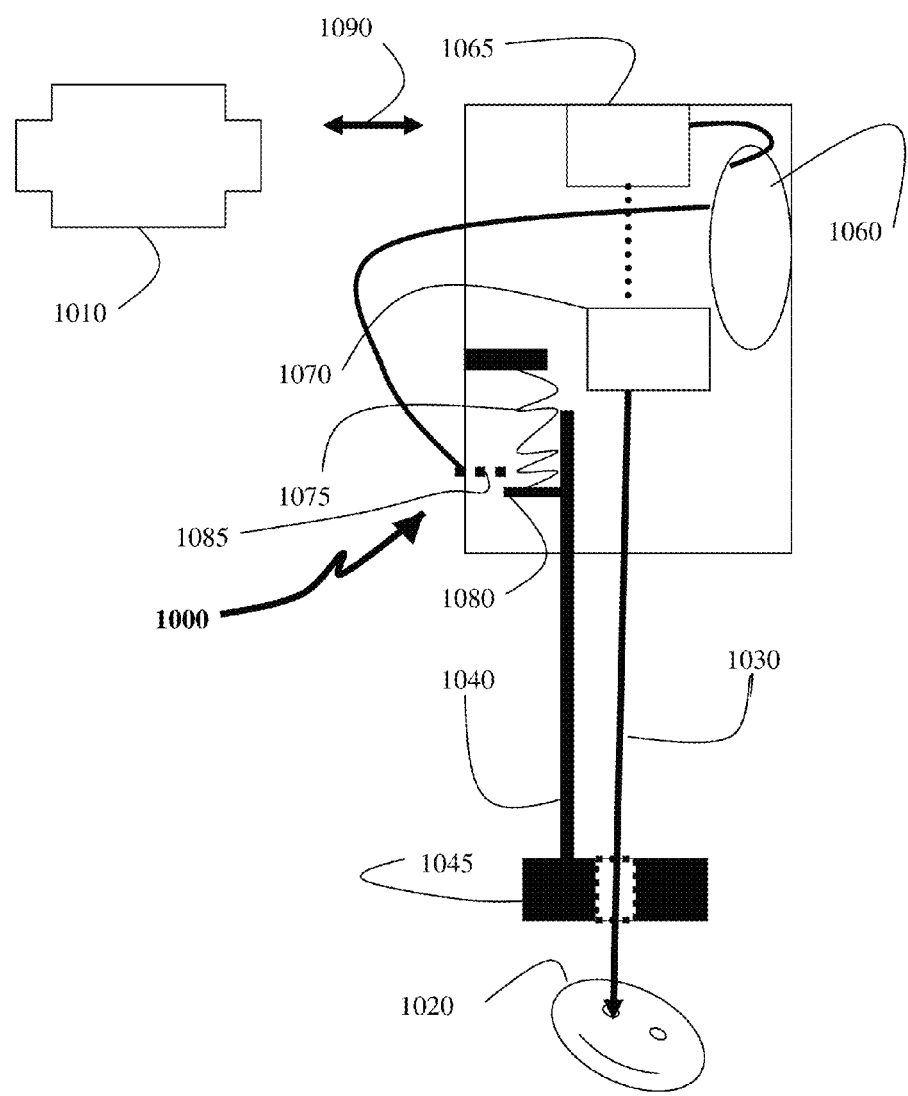
FIG. 1AA shows a sectional view taken through a device that can be attached (or operate alone) to energy or light or laser beam emitting device for the treatment of skin and organs.
Figure 1A:
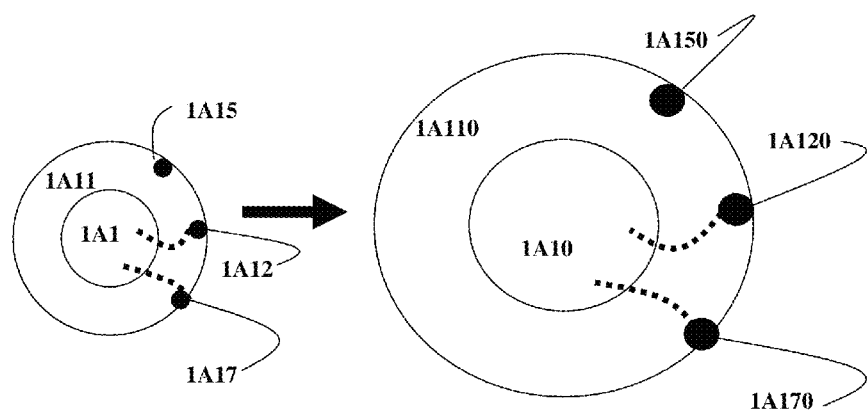

FIG. 1AA illustrates a preferred embodiment of the present invention and shows the components that this embodiment comprise of. It include a device 1000 that can be operatively coupled to any existing or contemplated medical or home use treatment device 1010 to prevent exposure of eyes or other sensitive skin 1020 or tissue to dangerous exposures of energy, 1030. The device comprise a member 1040, that extends at least partially into the path of the emitted treatment energy and prevents the emission of such energy unless the area about to be exposed to said emitted energy exert a physical force on the member, 1040. The physical force must be strong enough to cause a discomfort to injury-prone locations, 1020 such as, for example, eye, injured skin, injured tissue, or pain-sensitive parts of the body. Preferably the member may be coupled to a foot 1050, the foot exerts a blunt force on said target tissue or eye 1020 but such a force or pressure is not capable of causing injury to said target tissue or eye. The member 1040 is coupled to a circuit 1060, said circuit is operationally coupled to an emitter, 1070. The activity of the emitter is coupled to the movement of the member 1040. The emitter may carry its own power source or may be couple to a power supply or a battery power source or wall power outlet 1065. The member 1040 may have a hole in its foot 1045 through which the energy or 1030 or a carrier of mechanical energy such as a needle 1030 may pass towards the skin. The member 1030 is pushed by the force exerted on it by the skin 1020, it may face a resistance force exerted by a spring 1075 to control its motion. The motion of the member 1040 may, for example, cause a lever 1080 to activate a motion sensor 1085 operationally coupled to a circuit 1060 or a mechanical trigger 1060 that is couple to the activity of the emitter 1070, thereby causing the emitter 1070 to emit energy 1030 A preferred embodiment of present invention comprise a device that can be operatively coupled to any existing or contemplated medical or home use treatment device to prevent exposure of eyes or other sensitive skin or tissue to dangerous exposures of energy. The device comprise a member that extends at least partially into the path of the emitted treatment energy and prevents the emission of such energy unless the area about to be exposed to said emitted energy exert a physical force on said member. Said physical force must be strong enough to cause discomfort to injury-prone locations such as, for example, eye, injured skin, injured tissue, or pain-sensitive parts of the body.

Additionally and preferably, the present invention comprises systems, devices and methods in which a device has an emitter that emits a first energy along a path, a member that extends at least partially into the path and a circuit couples activity of the emitter with movement of the first member.

In an alternative preferred embodiment of the present invention, the present invention comprises systems, devices and methods in which a device has an emitter that emits a first energy along a path, a member that extends at least partially into the path and a mechanical coupler that couples activity of the emitter with movement of the first member.

All suitable emitters are contemplated, including coherent and incoherent energy sources, visible and non-visible wavelengths, and those that emit electromagnetic and/or other energy. Of particular interest are flashlamps, because they are inexpensive, and their energy is difficult to focus to a spot size that is likely to lead to retinal injury.

Emitters are preferred that have energy density of less than 30 J/cm$^2$, more preferably less than 20 J/cm$^2$, more preferably less than 10 J/cm$^2$, more preferably yet less than about 3 J/cm$^2$ and most preferably less than 1.5 J/cm$^2$. On the other hand, devices are contemplated that will be used for treatment of skin, and especially devices that can emit energies sufficient to cause damage to a retina of an eye. This includes, for example, laser hair removal treatment, laser skin rejuvenation, laser removal of tattoos, light treatment for acne, light treatment for hair reduction, laser or light treatment for removal of vascular lesions, and heat treatment for acne.

The member can have any desired size or shape, provided that the member can still serve as a interrupter not allowing the device to emit energy unless the member has been modified by the location targeted for treatment in a way that would cause discomfort to injury-prone locations such as, for example, eye, injured skin, injured tissue, or pain-sensitive parts of the body. For robustness, the member preferably has a length of no greater than 3, 4, 5, 6, 7, 8, 9, or 10 mm, depending in part upon the type of material, cross-section. There can be multiple members, which can operate independently from one another, or mechanically coupled in some way, for example by being coupled to a common foot. For example, the entire treatment window through which the energy pass to the target can serve as a member where the window, for example, has to be mechanically disturbed or pressed before energy can be emitted. Alternatively multiple independent members can operate independently. This mode of operation is useful in making it difficult for an inexperienced user (for example a child) to press all multiple members at the same time. If the device is designed so that energy is emitted only if all members position has to be modified simultaneously (for example, all members has to pushed in by at least 2 mm) then only a flat surface such as a target surface appropriate for treatment can cause such activation. The eye would be too sensitive to the touch. A child trying to push the multiple members with his fingers would find it difficult to coordinate such a multiple push without also at least partially blocking the beam.

The circuit preferably precludes the emitter from emitting the energy unless the first member is depressed. The amount of depression can be less then 5 mm and preferably less than 3.5 mm and most preferably less than 2 mm. An aiming beam is also contemplated, preferably one having a lower energy density, and/or a different wavelength from the main emitted energy. Said aiming beam can be on when the device is turn on and operate independently of the member that control the activation of the main beam because the aiming beam energy is substantially less powerful than the treatment energy that is designed to operate at power level sufficient for surgical or therapeutic purposes or at power levels designed to achieve tissue modifications or cosmetic improvements.

The invention also contemplates a second member so that the device control circuit also couples activity of the emitter with movement of a second member. The characteristics of the second member can be similar to that of the first member described above.

The invention also contemplates the possibility of the first and second members are coupled to a common foot. If both members are coupled to the common foot a better stability of operation may be obtained.

13. The device of claim 1, wherein the first member includes an expanded portion that absorbs at least 30% of the first energy.

The invention also contemplates the device discussed above with the first member being cooled to protect the surface of the treatment target, for example the surface of the skin. If the surface of the skin is subject to high treatment energy, the first member may be cooled so that when it is in contact with the skin it keep it cooled. For example, the surface of the skin may be cooled below 10° C., and preferably below 5° C. and most preferably below 3° C. In this embodiment the cooling element can be any cooled component capable of serving as a first member as described above but also cooled to so that upon contact with the skin it will absorb some of the skin temperature. For example, said first member can be passively cooled in a refrigerator or a freezer and brought to the desired temperature so it can bring the surface of the skin down to the temperatures described above. Alternatively and preferably, said first member can also be actively cooled.

The invention also contemplates using the first member of the device discussed above to incorporate an active cooling element capable of cooling the skin upon contact. In this embodiment, the cooling element can, for example, be made of similar material to those used in thermoelectric coolers (TEC) and incorporated into the first member. The cooling element can, for example, be made of TEC so it also serves the function of the first member as described above. The cooling element can further comprise active cooling element that actively cools the first member for example, a circulating coolant such as Freon-like gases can be used to circulate inside said member to actively cool first member.

The invention further contemplates incorporating the member of the device as a cooling element that has sufficient cooling capacity such that when the energy is applied at an energy density of at least 15 J/cm2 to a skin having an epidermal-dermal junction, the junction remains below 50° C. The invention further contemplates that that when the energy is applied at an energy density of at least 10 J/cm2, and more preferably at an energy density of at least 5 J/cm2 and most preferably at an energy density of at least 1.5 J/cm2 to a skin having an epidermal-dermal junction, the junction remains below 50° C.

The invention further contemplate that the cooling element is activated at a predetermined time subsequent to a detected movement of the first member. The amount of movement and required force on the member should be similar or greater to that required to activate the energy source. Thus, preferably, an activation of the energy source, also activates the cooling element. Most preferably, the movement of the first member as described above, should activate the cooling element prior to the activation of the energy source and the emission of energy. For example, the activation of the cooling element subsequent to the detection of movement of the first member should precede the activation of the energy source by about 1 second, and more preferably by about 0.2 seconds and more preferably yet by about 0.1 second and most preferably by about 0.05 second.

The invention further contemplates that the first member includes a fluid path through which a fluid is dispensed. For example, the foot of the first member can be hollow and contain, for example, a therapeutic fluid such as benzyl peroxide for the treatment of acne. Alternatively and also preferably, the fluid may be, for example, antibiotic for reduction of bacteria, or ALA compound to be followed up by a light dosage for a Photodynamic therapy (PDT) treatment. Most preferably the fluid can, for example, contain vitamin and minerals, or nutrient to nourish the skin or hydrate the skin. The fluid path within the member can be designed, for example, to include a series of perforation at the foot of said first member, said perforations are blocked by, for example, a membrane or a thin film that can be actively coupled to the device circuit so that the membrane or thin film are removed and allow flow of the fluid through the perforations and onto the skin surface upon detection of the movement of the first membrane.

Preferably the invention also contemplates that the first membrane that include a fluid path through which fluid can be dispensed includes a foot, wherein the surface of the foot of the first membrane is rough or contain shaper edges, for example edges that protrude beyond said foot surface from about 0.01 mm to 0.6 mm. Such a design will allow the foot to remove some of the skin upper layers as it contacts and moved across the skin surface, thus enhancing the delivery of the fluid contained within the first member or within the device across the surface of the skin and into the skin.

In a preferred embodiment the invention further contemplates that the first member includes a resistive heating element that allow heating of the surface of the skin. The resistive heating element may include a resistor capable of heating the surface of the skin to less than about 400 degrees centigrade, and preferably to less than about 300 degrees centigrade and more 200 degree centigrade, and more preferably yet to 150 degrees centigrade and most preferably to less than about 75 degrees centigrade. Preferably, the resistive heating element within the first member heat surface for a time duration of about 3 minutes, more preferably to a time duration of about 2 minutes, more preferably yet for a time duration of about 1 minutes, alternatively and also preferably for a time duration of about 1 minute or less, more preferably yet to a time duration of about 200 ms, and most preferably to a time duration of about 20 ms or less.

Preferably, the resistive heating element within the first member also include an insulating layer distal to the heating element. Said insulating layer may be composed of Teflon or polycarbonate or other suitable insulating element. Alternatively and preferably said insulating layer may also be transparent to the device energy, for example, made of polycarbonate, glass, or clear plastic. Alternatively and preferably, the insulating layer may be transparent to the device energy, electrically insulating but allow some heat conduction for example, made of sapphire.

From a method perspective the invention contemplate a method for treatment of skin ailment wherein energy is applied to a targeted surface but said energy is allowed to interact with the surface only if a step of disturbing a member actively coupled to the circuit that triggers the emission of the energy, takes place first. In this preferred embodiment takes the following steps: Aiming the energy generating source at the target area. Bring the energy generating source to the vicinity of the target area, allow a first member probe to interact with the target area, the interaction step then generate a feedback signal to the energy source that at a pretty determine level, for example, if the first member experience a force sufficient to, upon contact, cause discomfort to a human eye or injured area of the target skin, allow the final step of energy emission direct to the target area on the skin to take place.

In yet another preferred embodiment, the device the first member also prevent the device from contacting the targeted material. Alternatively and preferably said first member prevents the device from coming into a direct contact with the skin. This is important to avoid overheating of the skin if the window or lens allowing the energy to emerge from the device and into the targeted skin tissue become over heated as it is used to treat the skin ailment. Thus even without being cooled, possible heated device transfer of thermal energy is minimized due to first member preventing the device from coming into a direct contact with the skin.

The present invention also comprise a device that can be operatively coupled to any existing or contemplated medical or home use treatment device to prevent exposure of eyes or other sensitive skin or tissue to any form of dangerous or unsafe mechanical energy, for example, first member can be inserted in the mechanical energy carrier path, for example a needle, vacuum suction, dermabrasion, microdermabrasion, or a blunt mechanical energy carrier, to prevent activation of said mechanical energy carrier unless first member is moved to a predetermined level. Thus first member may for example, be actively coupled to mechanical energy carrier so it is not activated unless the first member is depressed by less then 5 mm with a force that is sufficient to cause discomfort to the eye or injured tissue. Alternatively and preferably, said first member may have to be pressed by less than 2 mm and most preferably less than 1 mm.

In yet further elaboration of this preferred embodiment, first member may be coupled to a foot. The foot is designed to contact the targeted skin. When the device is pressed again the targeted skin as described above, the emitted energy or mechanical energy carrier (for example a needle) is activated and pass through an opening in the foot to impact the skin. The pressure of said first member and the foot it is couple too is sufficient to reduce the amount of pain caused by said energy or mechanical energy carrier (for example a needle) as it impact the skin or target tissue. For example, the pressure the first member and the foot it is couple to preferably exert a pressure on the skin that is sufficient from stopping blood flow to the skin in order for said energy source to be activated.

In a further preferred embodiment of the present invention the circuit precluded the emitter from emitting the energy unless the first member is depressed by a force sufficient to reduce blood circulation in the skin above the mid-reticular dermis.

In an additional preferred embodiment of the present invention, the device include an energy carrier for example a needle and the circuit in the device preclude the needle from moving toward the skin unless first member is depressed by a force sufficient to reduce blood circulation in the skin above the mid-reticular dermis.

In an alternative preferred embodiment of the present invention, the present invention comprises systems, devices and methods in which a device has an emitter that emits a first energy along a path, a member that extends at least partially into the path and a mechanical coupler that couples activity of the emitter with movement of the first member In a preferred embodiment the circuit or mechanical coupler precluded the emitter from emitting the energy unless the first member is depressed by a force sufficient to reduce the sensation of pain.

Additionally and preferably, a method for treating tissue with energy is described, the method comprises: directing the output of an energy emitter towards a tissue; extending a first member at least partially into the path the energy would follow between the energy source output and the target; coupling the activity of the energy with the movement of the first member.

The device described herein utilize light energy, heat energy, or a combination of the two for selective surface heating that allows the user to achieve temporary pore enlargements for cleaning of the skin pores and expulsion of unwanted debris and undesired substance filling the pores, thus reducing the size of unseemly pores and enhancing the health and appearance of the skin. The method also contemplates thermal energy and light energy deposition into the skin to allow selective injury to the upper layers of the skin and new more elastic collagen production. The devise described herein is also designed to allow treatment of the skin more effective with possibly with lower doses of rejuvenating agents. The controlled damage to the epidermis and upper layers of the dermis, that result in new collagen production, and "Top and bottom" action via the use of a combined optothermal action through enhanced absorption due to a heating element at the top or action of an absorbing substance at the top and optothermal light to thermal energy conversion throughout the target skin volume.

The present invention describes a safety device that can be attached to any laser, light or energy based therapeutic device. It can also be attached to any energy emitting diagnostic or imaging devices if the emitted energy pauses danger to the eyes or to sensitive tissue or skin on a human or animal body that can be damaged. The invention described herein can also be attached to any mechanical or thermal or other medical device that can, upon contact with the eye or sensitive tissue pose danger or cause damage to said eye or sensitive tissue or skin area.

a compact hand held device that can be safely used by adolescents and adults wishing to improve the texture and appearance of their skin and to minimize the appearance of acne, blemished skin, or fine wrinkles.

It is an object of the present invention to provide a device and method for treating skin conditions, reducing the appearance of fine lines and wrinkles, and clearing skin from blemishes and pigmented spots. Another object of the invention is the reduction, management and control of hair on the surface of the skin.

Another object of the present invention is to provide a hand held device that can be used safely to treat with light or heat or both a controlled amount of tissue and in particular to achieve one or more of the following: skin tissue to allow skin rejuvenation, hair removal, hair reduction, hair management, fine line reduction, collagen regeneration without collateral damage or excess damage adjacent tissue while enhancing skin condition and appearance.

In one embodiment, the present invention comprises a hand held device with an on/off switch and a button that allow the device to emit pulsed energy to treat the tissue in contact with the device. In this embodiment, to ensure that the device is activated only when it is in contact with the skin, one or more protruding guards (PG) extends in front of the treatment head and allow activation of the device only when all the PG are fully pressed to a predetermined level. This feature is specifically designed to ensure that the device is NOT activated when placed in front of the eye or other sensitive skin or tissue locations. For example if the device is placed in front of the eye, the protruding plastic or metal guards (or any other material from which we make the PG) will cause the eye to close instinctively. The idea is that the pressure or contact in particular mechanical contact of a rigid physical object with the eye or sore or damaged skin or tissue, would cause a sensation of pain or discomfort, would cause the treated person to jerk away or remove or object to the contact. If the device can be activated ONLY after a firm contact and mechanical pressure has been established between the device's PGs and the target tissue, the patient or person subject to the intended treatment would not willfully or unconsciously allow the device to be activated and the treatment to proceed, thus the treatment subject or patient will not allow damage to such sensitive target area to occur.

Obviously the aim of the device is to treat the skin not the eye. But if one is not wise enough to avoid aiming the device into the eyes, the device will not fire and not emit its energy (thermal or optical, or otherwise) unless it is in close contact against the skin and the PG pushing against it. Obviously sensitive locations like the eye will instinctively close to avoid the touch. Also areas with skin burns or skin ailment will become uncomfortable under contact with the PG, and one will not want to push the PG against these skin locations, and certainly not push very hard at these locations, thus not allowing the activation of the device.

When it is placed on a healthy tissue, the plurality of PGs are pressed in and the device is allowed to fire. A battery within the device powers a circuit board and drives a short pulse of current through a resistor to allow the generation of a heat pulse. The thin film resistor heats up with sufficient energy to cause skin rejuvenation and induced a biological response improving the appearance of the skin. Typical energy delivery time duration is less than about 3 sec. Optical and thermo-optical energy are responsible for tissue targeting although chemical processes (such as PDT) as well as optical or thermal induced mechanical processes. Optical, thermal, chemical or mechanical responses in the tissue induced by a flash lamps or thermal energy generator together with a protruding guards that allow activation only in tissue safe areas a biological response that enhances skin appearance.

The total heat energy transferred is low enough to prevent burns, typically less than 50 J/cm2 and for most applications less than 10 J/cm2. For consumer applications an energy density of less than 2 J/cm2 is contemplated and preferably less than 1 J/cm2.

In another embodiment, of the present invention an electrical energy source is used to generate thermal pulses of energy. In yet another embodiment an optical absorbing layer that is heated by flash lamps within the device is used to create thermal pulses. The flash lamps are fired by a short discharge, which produces broadband light. Such light can be filtered to produce specific absorption and specific tissue effects such as photothermolysis. Depending on the desired final temperature of the optical absorbing layer one or multiple flash lamps can be fired simultaneously to combine their light under a single reflectors directing the light into the target skin. Alternatively, lamps can be fired in sequence to result in broader longer pulse duration of energy. Again, thermal conduction transfers the heat to the skin and causes a biological response that enlarges pores to enhance product or medicine delivery, clears acne, induce rejuvenation of the skin, and produce new collagen. The total heat transferred is low enough to prevent burns, typically less than 50 J/cm2 and for most applications less than 5 J/cm2. In this embodiment, the absorbing layer can be designed to allow some light to be transmitted. For example, blue or UV light could be transmitted to interact directly with tissue and kill bacteria directly.

Expending Universe Skin Treatment Model (EUSTM)

One object of the present invention is to provide a device and method for treating acne as well as inserting and removing material from the skin. To accomplish this the invention contemplates in a preferred embodiment heating up the top layer of the skin so it expends. The expansion of the skin or a portion thereof, (for example the top layers of the skin such as the epidermis, epidermis and dermis and epidermis and a portion of the dermis) causes a relative displacement of every point on the skin with respect to an adjacent point. Such an expansion, similar to the expansion of a balloon or the theory of the expanding universe, results in enlargement of pores and breakup of intercellular, and interlocking substance plugging pores or opening on the skin, and in increased skin porosity. Note that unlike prior art that used to heat up the skin for the purpose of ablation, or natural occurring heating of the skin through hot baths or hot compresses, sunlight or space heaters, the heating of the skin contemplated by the present invention is design for the purpose of achieving sufficient heating of the top layers of the skin so that its expansion result in pore opening and increase skin porosity but not in damage to underlying viable tissue or irreversible damage to the skin or ablation or removal of skin components.

Figure 1:
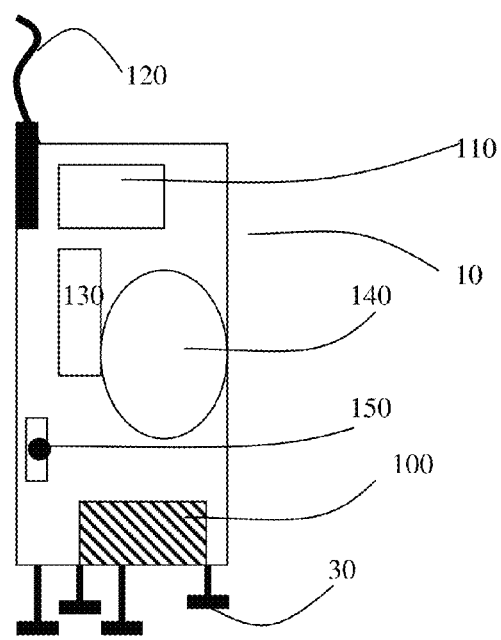
FIG. 1 shows a sectional view taken through a device for enhancing safety of skin treatment with energy
Figure 11:
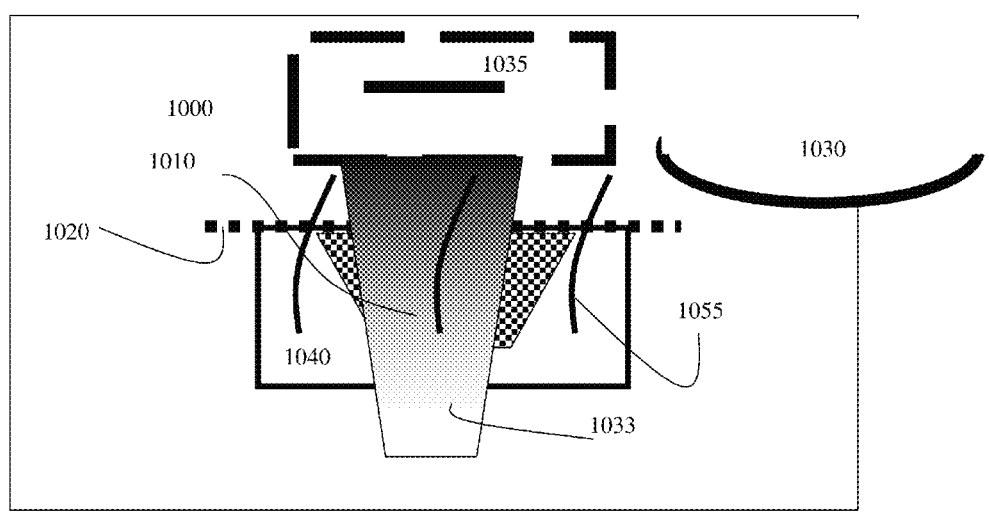
FIG. 11 shows the application of energy to activate topical fluid delivered to the skin

Expanding universe model (EUM) for treatment of skin conditions and acne: FIG. 1a illustrates such an expansion of the skin; the increased of distance between each and every adjacent point on the skin surface and the resulting opening of pores and other surface skin structures. In the figure, a preferred embodiment of the desired effect contemplated by the invention is described and the way to achieve this effect is also described in the following preferred embodiment. In FIGS. 1a, 1a1 and 1a11 are schematic representation of the dermis and epidermis respectively. The locations on the surface of the epidermis, locations 1A17, 1A12, and 1A15 are separated, for example by, for example, 5 mm on the surface of the epidermis. If for example rapid heating of the skin is achieved by, for example, an electric, electromagnetic, light, or microwave heating of the skin, the skin will expand rapidly, like a balloon to the dimensions shown in the left side of the arrow, dimensions shown in 1A10 and 1A110, for the dermis and epidermis respectively. The spots 1A17, 1A12, and 1A15 will now be further apart, for example, separated by a linear distance of, for example, 10 mm. The new locations are represented by 1A170, 1A120, and 1A150. Clearly, if the locations 1A17, and 1A12 for example represent the initial position of two opposite ends of the pores, the new locations 1A120 and 1A170 represent an expanded pore whose diameter is now about twice as large and thus its surface opening is 4 times as large. Note that to relieve liquid pressure due to sebum build up even a few microns of increased pore opening diameter will suffice. Similarly, an increased in the pore opening diameter of only a few microns is sufficient to allow the enhanced penetration of liquid or fluids into the epidermis in to even to the dermis.

The object of the present invention is to provide a device and method for treating hair and various skin conditions and ailments. For example, the device may be used for hair removal or reduction of hair follicle counts, treatment of psoriasis, acne, (active acne, pimples, or scars) reduction of wrinkles, fine lines, skin lesions, and/or general improvement in the appearance of the skin. Another object of the present invention is to provide a device that can be used safely to treat a tissue without undesirable injuries to the skin. One of the features of the present invention is a mechanism to ensure that only healthy and indented tissue targets are treated. For example, both in the professional office (Physicians, dermatologists, Plastic surgeon, Aesthetician, hair dressers, cosmetologists, nurses, Ob:GYN) and for consumer use, there is an important need to ensure that no light or other form of energy would be applied to sensitive targets such as the eyes, or tissue and skin sites that are sensitive or injured. The present invention provide for such a mechanism.

By utilizing a protruding guards or protruding arms that control the activation of the energy source, the protruding arms can prevent firing of the energy source unless they are (all or part of them) physically depressed to a certain level. The idea is that a sensitive target like the eye or the surface of the eye will not support that kind of mechanical pressure by the protruding guards (PG). Furthermore, the eyelids instinctively shut or close when in contact, or even when approached by a mechanical object.

Such PG can be made of transparent material to minimize light energy source in the case of light energy use (Lasers, IPL, Flash lamps, LEDs, or other light sources)

Such PG can be made of cooled components or cooling parts to also serve to protect the epidermis from injury. For example they can be made of Peltier Cooler/thermoelectric cooler (TEC) so that they can cool the surface of the skin as they make contact. The polarity of the Peltier coolants can be quickly reversed so that these PG can be used alone or in combination with light or lasers, or RF or Microwave sources, to heat and treat the surface of the skin or tissue.

In a preferred embodiment the energy from the device is not able to be applied unless and until the PG are depressed to a predetermined level.

The requirement of depressing the PGs is important for at least two reasons:

The eye or sensitive or injured area of the skin or tissue, will not tolerate the contact and thus no activation of the energy source is possible and no injury will result The contact and depression of the PG require the output window to be spatially in close physical proximity to the skin or tissue surface or whatever the target is. This, in the case of light, lasers or any other EM energy or thermal energy or radiative energy source, means that the energy is not spread over a large surface area but is directed and intercepted quickly with the intended target surface.

In FIG. 1 a Hand Held Home Use Hair treatment device generally includes a flash lamp 100 is powered by a battery 110 or a power plug 120 which charges a capacitor 130. The lamp 100 is willfully triggered and controlled through the use of a control board 140 and an activator switch 150.

The lamp 100 (or any other energy source) is housed in the consol 10 and its operation is also controlled by plurality of guards 30. the protruding guards are protruding out of side of the device 10 facing the skin or the human body. The guards 30 are connected to the controller of the lamps and do not allow the lamp to fire unless they are ALL depressed to at least a predetermined depth. For example the predetermined depth can be such that the lamp is in close enough proximity to the target tissue or skin so that most of the light from the lamp 100 can not escape sideways and is only directed forward towards the skin. The energy source 100 can be laser or light source, flash lamps, LED, RF, Microwave, any kind of Electromagnetic (EM) energy source, any kind of radiative EM, energy source, thermal energy source, or thermal cooling source (negative or out of the target area flow of energy) energy source.

Only when all protruding guards 30 are full depressed can the flash lamp fire. This arrangement prevents accidental firing of the lamp into the eye.

The Protruding guards 30 can be made of transparent material such as, for example, plastic or glass. The idea is that a protruding guards (PI) array 30 will ensure that the eye is closed PRIOR and BEFORE firing of the lamp.

Figure 2:
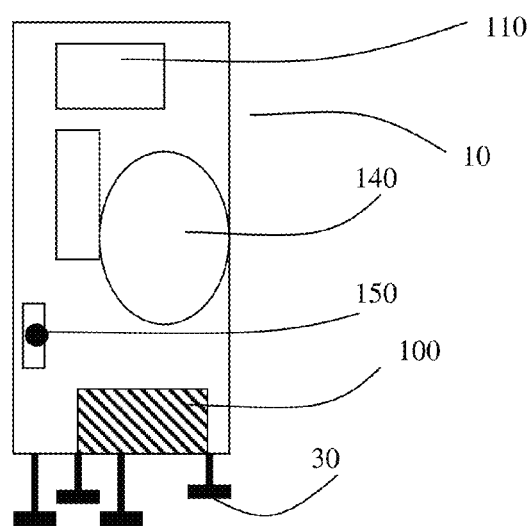
FIG. 2 shows another sectional view taken through a device for enhancing safety of skin treatment with energy.

FIG. 2 shows the same device as in FIG. 1 except that the protruding guards (PG) 30 are made of transparent material to minimize intercept of energy. By making the protruding guard 30 from transparent material, the energy from the source can travel with minimal interruption, minimal scattering and minimal absorption down the path towards the skin or target material. The PG 30 may also be made of substance capable of cooling the surface with which it is in contact so allow protection of the epidermis, further energy control, energy removal from the target tissue or surface being treated.

Figure 3:
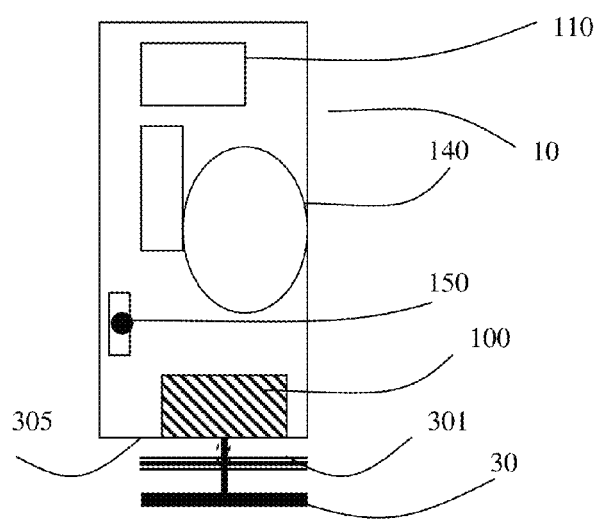
FIG. 3 shows another sectional view taken through a device for enhancing safety of skin treatment with energy

The PG 30 may also be made of both transparent substance which is also capable of cooling the surface with which it is in contact so allow protection of the epidermis, further energy control, energy removal from the target tissue or surface being treated FIG. 3 shows the same apparatus as in FIG. 1 except that instead of a plurality of protruding guards PG only one is being used, 30. the protruding guard can have all kind of desired properties: It may be made of cooling (active or passive cooling) so as it is pressed against the skin it also cools. It may be made of transparent material to allow more energy to get into the skin. It may be made of substance or mechanism capable of heating or energizing the skin or delivery energy into the skin. It may be made of absorbing material so that as it is being pressed against the skin it also absorbs energy generated by a light or lasers or any other EM Radiative energy source to absorb the energy and conduct it further into the treated surface or targeted surface.

A predetermined "press Level" i.e. the amount of physical depression in of the protruding guards PG in the direction of the arrow, can be determined and built into the device. FIG. 3 also shows such a pre-determined depression of the PG, 301, before they allow activation of the device. Such a displacement in the PG extension out of the treatment head surface 305 can be built into the device to prevent firing before the device is brought to such predetermined proximity to the surface of the target area. The PG can also have a maximum "collapse distance" or press-distance where the PG can then prevent a contact CLOSER than the predetermined level.

The above descriptions and illustrations are only by way of example and are not to be taken as limiting the invention in any manner. One skilled in the art can substitute known equivalents for the structures and means described. The full scope and definition of the invention, therefore, is set forth in the appended claims.

Figure 4:
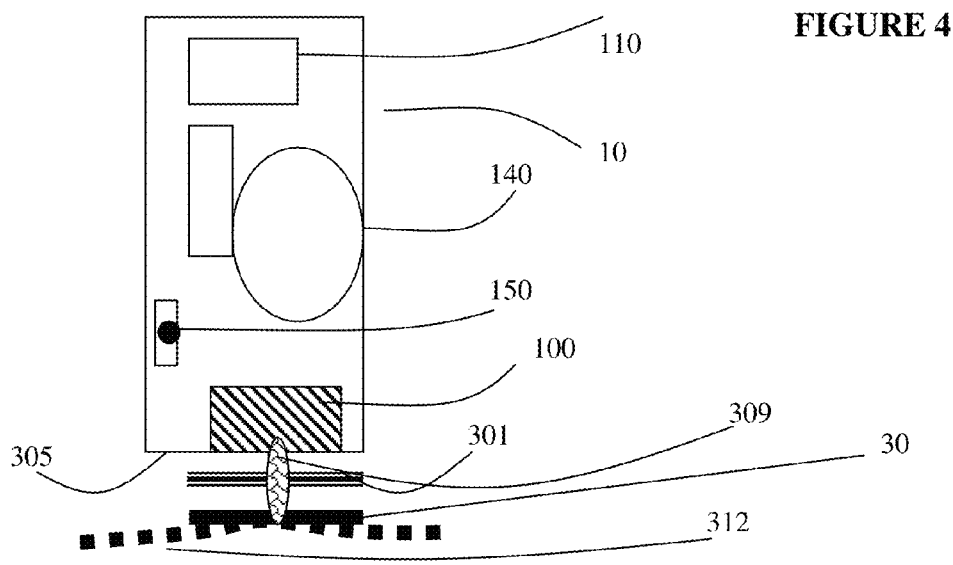
FIG. 4 is another sectional view taken through a device with a member and a foot to enhance safety of skin treatment.

FIG. 4 also shows the device contemplated by the present invention with the inclusion of a spring loading 309 to ensure that the Protruding guards (PG) return to their un-depressed position once the device is removed from contact with the skin. It also shows the skin 312 in beginning to make contact with the PG in its initial extended position.

Specification and Further Preferred Embodiments of Various Components of Device with PG In further embodiment the invention contemplates a device for reducing the presence of hair on the body, the device may comprise a light source, laser source, or any other source of electromagnetic energy, or other form of energy directing its energy towards the surface of the skin, a plurality of protruding guards extending from the device surface towards the skin surface, the protruding guards do not allow energy source activation unless they are pressed to a predetermined level so that the entire device is sure to be in close proximity to the surface of the skin and the protruding guards are in contact and apply pressure to the surface to be exposed to the source energy, In a preferred embodiment the device above may further comprise a cleaner to clean the target area on the surface of the skin, a an substance capable of absorbing at lease some of the energy of the hand held light source, A massager or substance driver capable of massaging the substance on the target area of the skin or driving at least some of the substance into the skin, a cleaner capable of cleaning the target area on the surface of the skin a light activator capable of activating the handheld compact light source In further preferred embodiment the device above may further comprise a conditioner-containing component capable of applying conditioning creams, lotions, or any other substance to enhance the skin appearance and condition.

In a preferred embodiment the invention also contemplates a method for reducing the presence of hair on the body, the device comprising: Removing the hair from the target area on the surface of the skin targeted for treatment, Cleaning the target area on the surface of the skin Applying to the target area of the skin a substance capable of absorbing at lease some of the energy from a handheld light source, massaging the substance on the target area of the skin cleaning the target area on the surface of the skin, Activating the light source from the handheld light source In a preferred embodiment the method above further comprises a substance capable of enhancing the skin condition and enhancing the skin appearance.

In a preferred embodiment the device above may further comprise wherein the light source is a flash lamp.

In a preferred embodiment the device above may further comprise at least some of the absorbing substance is allowed to remain on the surface of the skin and is not cleaned off.

In a preferred embodiment the device above may further comprise a massager which is an instrument capable of generating mechanical vibration In a preferred embodiment the device above may further comprise the massager above which is capable of generating mechanical vibration or function as an ultrasound source of energy.

In a preferred embodiment the device above may further comprise the massager or substance driver mentioned above which is also a thermal element capable of heating the skin to a predetermined temperature range and a predetermined range of lengths of time.

In a preferred embodiment the device above may further comprise the massager or substance driver which is an opto-thermal element.

In a preferred embodiment the device above may further comprise the opto-thermal driver element which us a handheld light source energy which absorbed by a layer of substance or a film capable of absorbing the light energy.

In a preferred embodiment the method discussed above may further comprise an absorbing substance which is driven into the skin by a mechanical massager or an ultrasound. The method of the preferred embodiment contemplated above may further comprise the absorbing substance being driven into the skin by opto-thermal means. This preferred embodiment may further comprise the absorbing substance being driven into the skin by placing a high absorbing film in contact with the skin and illuminating the high absorbing substance with a light source.

Preferred embodiment may further contemplate the absorbing substance being driven into the skin by thermally heating the surface area. Alternatively and preferably the method of the present invention may contemplates the absorbing substance is driven into the skin by heating the skin area to a predetermined temperature range and a predetermined time duration.

In a preferred embodiment the contemplate a device for controlling hair growth comprising: an optical element with variable power levels, at least one light source, a circuit to deliver a fixed amount of energy to the plurality of light sources, means to activate and trigger circuit.

The device further contemplates the circuit capable of delivering a predetermined amount of energy to the plurality of light source also allows the user to adjust the light source power level such that no permanent damage or alteration occur to any living tissue in the target skin.

The invention further contemplates a device for reducing the presence of hair on the skin, the device comprising: A handheld compact light source. A circuit to deliver a predetermined amount of energy to the light source, A trigger to activate and trigger the circuit. In a preferred embodiment device above would have a flash lamp as a light source of energy or an LED as a light source of energy. A preferred embodiment may also contemplates an applicator capable of applying a substance which is capable of absorbing at least some of the light source energy prior to light activation. Furthermore, the applicator capable of applying a substance which is both absorbing at least some of the light energy and thermally conduct the absorbed energy down the hair shaft.

How the Widows are Made

Figure 5:
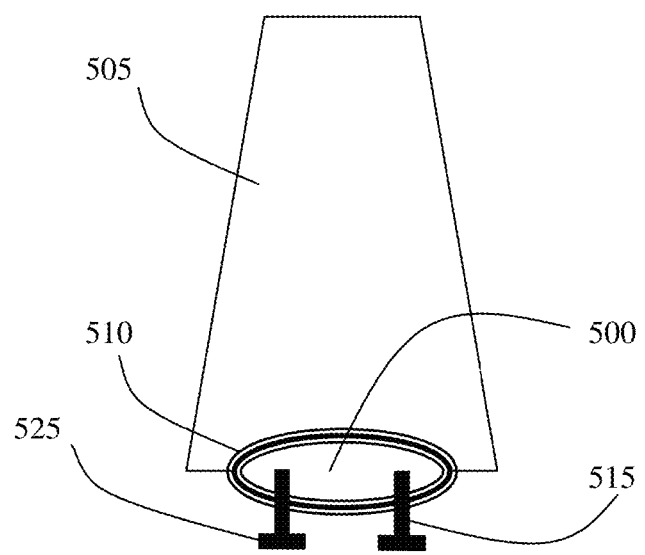
FIG. 5. is a sectional view illustrating plurality of safety members and feet.

In yet another preferred embodiment shown in FIG. 5 the device for treatment of skin conditions and hair treatment incorporating a treatment head. The device includes a plurality of windows 500 for the sources radiation or energy to flow therethrough onto the skin surface. The treatment head also incorporate a frame 510 to mount the window into the treatment head body 505. A plurality of protruding guards (PG) 515 is made of rods 520. The rods 510 can be made of metals, for example, aluminum or stainless still, or plastics, for example polycarbonates (such as the commercial brand Lexan), or Teflon, and preferably made of biocompatible material.

The protruding guards are connected to a contact base 525, which can be made wider than the rods to make for a lower pressure on the skin (since pressure is force over area and the area of the foot plate ca be made larger) and a more comfortable contact.

Figure 6:
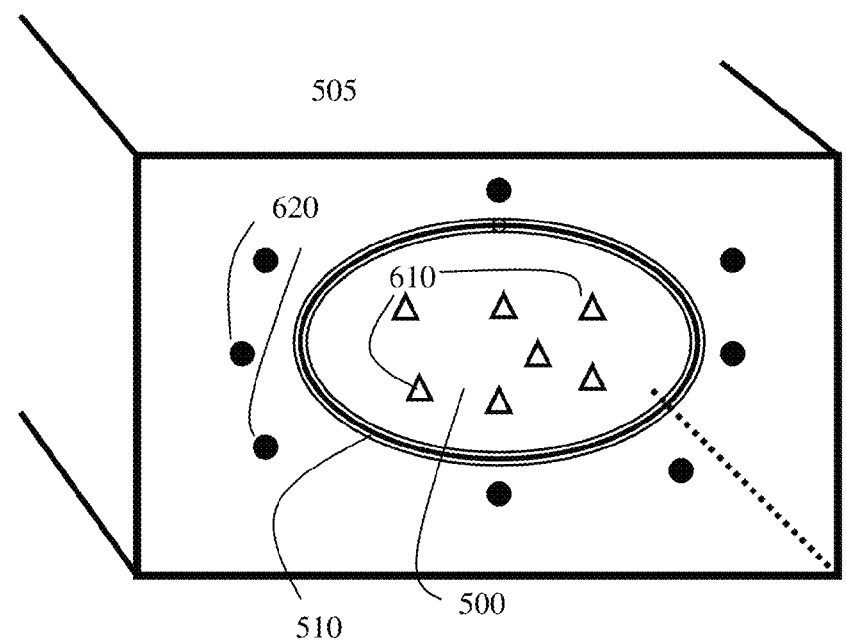
FIG. 6. illustrate various possible placement position for safety-enhancing members.

In a preferred embodiment, the invention contemplate using protruding guards in the following locations on the device output tip. These locations are shown in FIG. 6.

The protruding guards, 610 can be mounted in around the window 500 as shown by the triangles, 610, (for example in the middle of window 500, as sown by the triangles 610), or even to form a shield around the window 500, (the shield is shown by 510), wherein the shield 510, plays the double role of BOTH interlocking and preventing operation of the device UNLESS the shield, 510 is fully pressed to a predetermined level, AND, shielding and preventing radiation from coming out through the side of the window (i.e. so that all radiation is directed into the target skin and substantially other radiation is prevented from leaking or propagating sideways into the eye or other unwanted directions). Alternatively additional protruding guards (PGs), 620 can be placed around the window.

Figure 7:
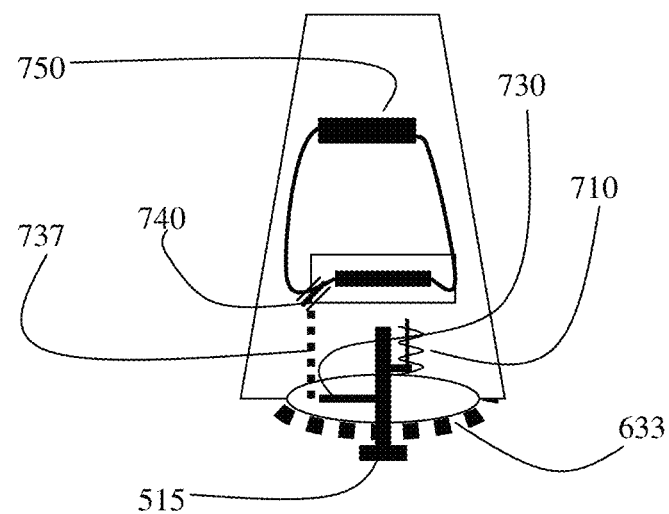
FIG. 7 shows a sectional view taken through the device for enhancing safety of skin treatment showing possible safety interlock position.

FIG. 7 shows another preferred embodiment for the protruding guards contemplated by the invention. The PG can be mounted with coiled springs 710, or spring loaded mount so that the springs push back on the PG when the PG are pushed by the contact with the skin. This allows the PG to be ready for the next use as soon as the treatment head is lifted off the surface of the skin and the PG is ready for the next use.

An example of a possible preferred embodiment of the interlocking that prevents the energy source (for example, a plurality of flash lamps, 730), from firing, is also shown in FIG. 7. When the PG 515, are pushed back by the pressure generated from a contact with the skin, they force a lever 737 to push a switch 740 that close a circuit 745. The closed circuit in turn, allows the discharge current to flow from a plurality of capacitors 750 to the energy source, 730, for example, the plurality of flash lamps, 730.

Figure 8:
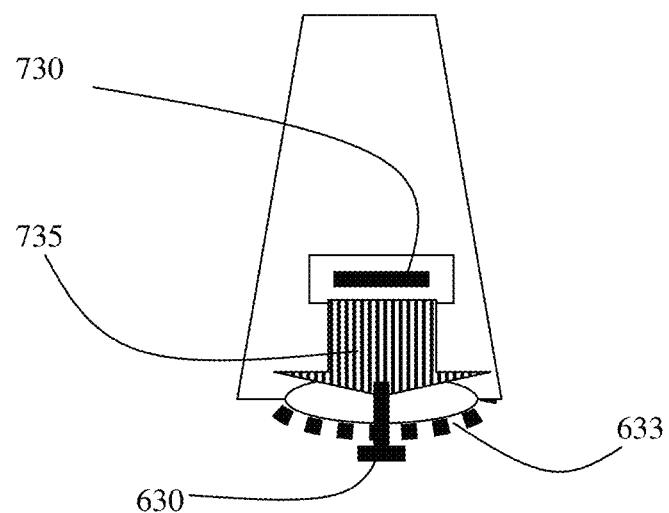
FIG. 8 shows possible placement of the member in the pass of the beam.

In a preferred embodiment shown in FIG. 8 at least one protruding guard, PG, 630 is positioned IN the light or radiation pathway 735, the PG 630 must make a firm contact with the skin so that unless it is pressed to a predetermined level the light or energy source can not be activated.

In a preferred embodiment at least one protruding guard, PG, 630 is positioned IN the light or radiation pathway 735, the PG 630 must make a firm contact with the skin so that unless it is pressed to a predetermined level and create a minimum of pressure on the skin, eye, tissue, or any target material it is in contact with the light or energy source CAN NOT be activated. the pressure exerted on the eye, skin or any target material must be AT LEAST of sufficient magnitude to cause discomfort in the, eye, skin or tissue if it injured, suffer from lack or damaged epidermis, or is susceptible to injury. Also, the pressure at the target material must be AT LEAST of sufficient magnitude to cause discomfort in the eye, if it is place over the eye or in the vicinity of the eye or tissue if it injured, to create a response of wanting to close the eye, to create a response of wanting to remove the object form the eye, or both.

Figure 9:
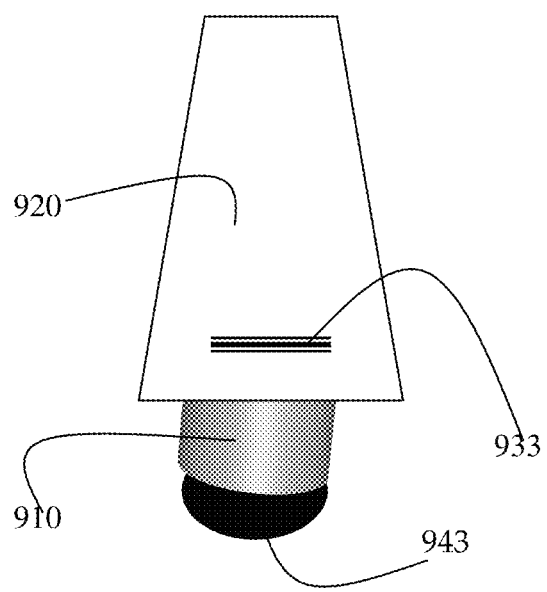
FIG. 9 shows how the entire window can serve as a safety enhancing member

In a preferred embodiment shown in FIG. 9, the entire window 910 serve as a protruding guard by being capable of being pushed into the device. The whole window is physically pushed inward by a pressure greater than that required to cause pain on sensitive skin or to trigger eye lead closing reflex. The lamp 933 or any other energy source in the device 920 will not fire unless the window is pushed to a predetermined level. Alternatively, a film or filter 943 in front of the window may serve as a protruding guard if we require that such a film or filter will be pushed into a full contact with the window before the device energy source can be activated.

Alternatively and preferably the window or lens 1080 may be made with compartments 1083, containing fluid to be dispensed during operation of the device to apply topical fluid to the target skin.

Figure 10:
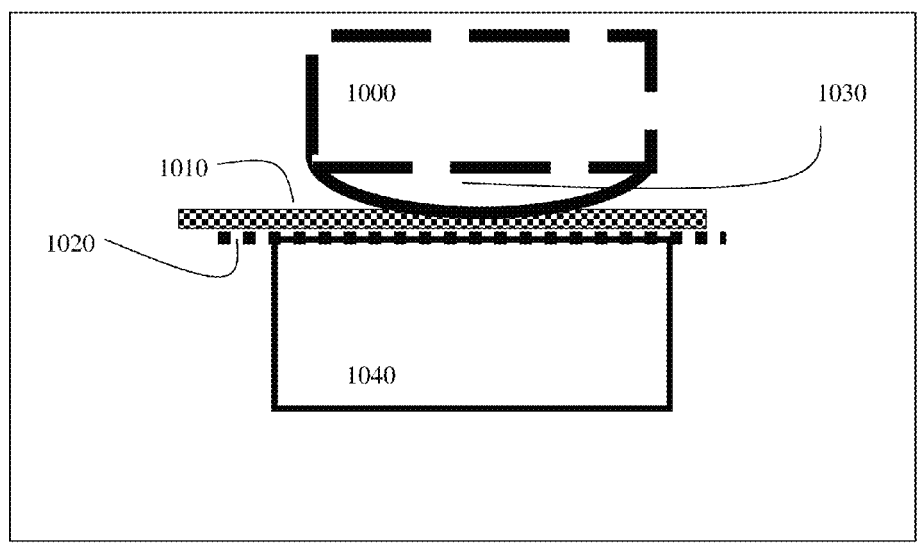
FIG. 10 shows a cross sectional view taken through the delivery head showing a method and device for storing dispensing and applying topical fluid to the skin.

In another preferred embodiment shown in FIG. 10 the invention contemplates a device which is capable of first delivering a product through the epidermal and possibly also through the dermal barrier and then activating the delivered product when the HAS film has been removed and a does of light is delivered to the tissue in a subsequent step.

For example, the preferred embodiment shown in FIG. 10 illustrates the delivery of a substance capable of retarding hair growth and then delivering a dose of light to activate the substance and enable the action of the substance reducing hair growth.

This is shown in FIG. 10: In this preferred embodiment, a substance capable of promoting hair growth (for example, minoxidil (brand name: Rogaine)) may be applied to the surface of the skin and then delivered with the enhanced action of the present invention optothermal delivery device. Alternatively and also preferably a hair growth prevention compound or medicine such as those used in photodynamic therapy (PDT) and light combination hair reduction therapy (for example a compound such as those known as ALA) may be applied topically to the surface of the skin and then may be applied to the surface of the skin and then delivered with the enhanced action of the present invention optothermal delivery device. As described elsewhere in the specifications, the rapid loading of thermal energy at the surface of the skin results in the expending universe skin treatment model (EUSTM). The EUSTM allow the pores and other skin openings (for example inter-cellular spaces) to expand and open thus allowing enhanced products, compounds, or medicine delivery into the target tissue or organs (for example, hair roots or hair papilla or hair matrix feeding the hair follicles).

Alternatively and preferably, the present invention contemplates also delivering substance capable of modifying or damaging the function of other targets in the skin such as sebaceous glands or fat tissue cells, or any other organ or tissue under the skin surface we desire to modify.

As shown in FIG. 10, subsequent to the delivery phase, the tip on the device may be changed to a transparent or partially or fully transmitting tip, capable of transmitting the energy or light itself into the skin. The device is activated to deliver a dose of light or other form of energy that is capable of activating the delivered substance in order thereby retarding or eliminating hair growth or modifying the function of the targeted tissue or organs under the skin. The sequence of action, device and method are shown in FIG. 10.

As the figure shows, a substance capable of enhancing the retardation of the hair growth 1010, is applied to the skin surface, 1020, the device contemplated by the present invention, 1000, equipped with an opto-thermal delivery head, 1030. The opto-thermal delivery head 1030 is capable of converting input energy, preferably, but not limited to electromagnetic energy, into heat, the heat energy result in rapid energy deposition of energy into the skin surface 1020 and expansion of the skin surface 1020, the thermal energy, subsequently, allow the hair growth retarding substance 1010 to better penetrate the surface of the skin 1020 and enter into the epidermis and dermis 1040.

FIG. 11 shows the next step in such a preferred embodiment, wherein the opto-thermal delivery head 1030, is removed, the light 1033 or electromagnetic (EM) energy 1033 from the energy source is allowed to penetrate the skin 1040, where the substance capable of retarding hair growth 1010, has now penetrated deeper into the skin 1040, and into the vicinity of the hair follicles 1055. The light or EM energy then either activate the hair growth retarding substance, 1010, or enhance hair growth retarding effects of the light or EM energy itself or, both (i.e. the light or EM energy BOTH help retard hair growth, AND enhances the effect of the hair growth retarding substance).

In yet another preferred embodiment a layer of substance such as hair wax is used to cover the surface of the skin including the hair on the skin surface.

The hair is then pulled out of the skin in the process, removing the substance that is covering the surface of the skin (for example a layer of wax) from the vicinity of the hair follicle opening. In a preferred embodiment, the layer of substance covering the surface, for example wax, may also be highly reflective. When the hair is pulled out of the follicles, it removes with it some of the substance or was leaves a relatively absorbing regions so that when light or energy is directed to the surface of the skin, most of the energy is reflected from most of the regions of the skin and only energy or light impinging on the regions in the vicinity of the removed hair follicles, where the reflective substance has been removed, is absorbed by the skin, penetrate the skin and propagate further down the skin towards the targeted tissue or organ such as hair papillae, hair roots, or sebaceous glands.

Opto-Thermal Treatment Head for the Conversion and Coupling of Energy

Opto-Thermal Coupler for Flash Lamp Acne Treatment Device:

Opto-Thermal Coupler—Intense Pulse Opto Thermal Wand

The purpose of the following preferred embodiment of a device is to allow an efficient consumable, consumable intermediate element that allows conversion of energy from a low cost source of energy, into one tailored for use in dermatology and in treatment of skin conditions.

Figure 12:
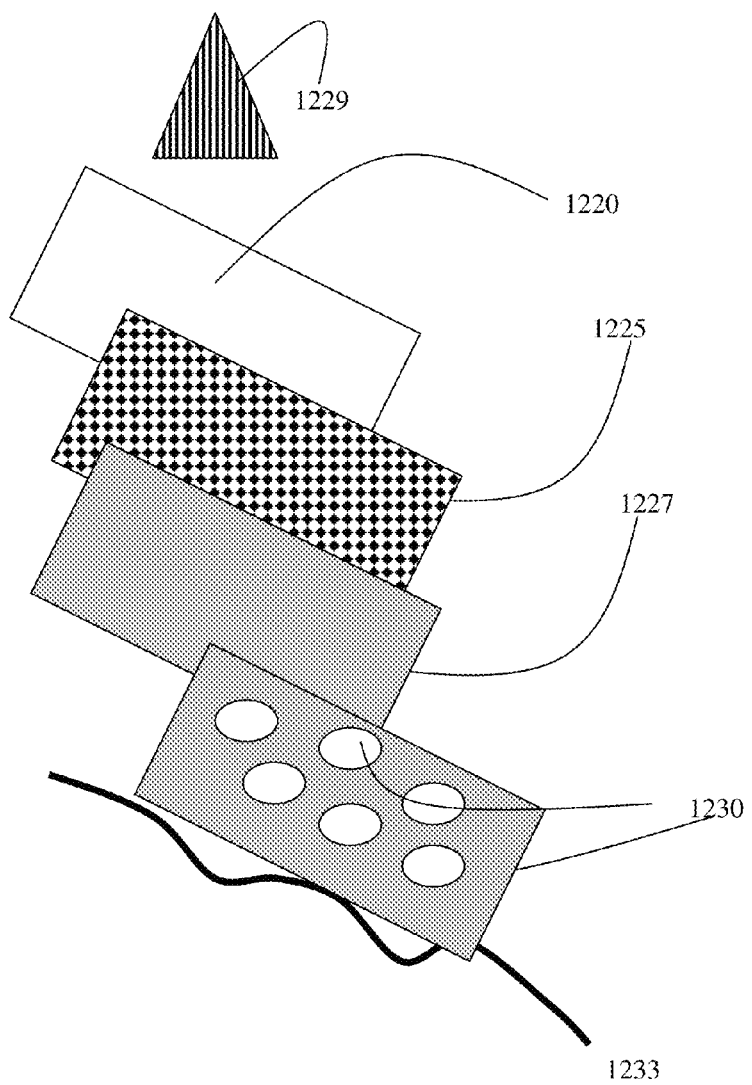
FIG. 12 shows components of the device necessary to accomplish energy conversion.

FIG. 12 shows in a preferred embodiment the components of the device to accomplish such energy conversion. It include an intermediate medium, for example a plastic window or glass slide 1220 with thickness ranging form about ¼ of an inch to about 1 mil (about 20 micrometer) and preferably with thickness ranging from about ¹⁄₆₄ of an inch to ¹⁄₃₂ of an inch.

The slide can be made of Mylar, polycarbonate, or glass, and preferably from a material that is substantially transparent to electromagnetic radiation in the range of from about 350 nm to about 3 micrometer and preferably in the range of about 400 nm to about 1200 nm, but blocks out harmful UV radiation. For example, a substrate of polycarbonate material may be used.

A further elaboration of the present invention contemplates a third layer, 1225, of high absorbing substance deposited onto the window layer 1220. the high absorbing layer can be made of metallic substance machined or modified to absorb at least some of the radiation in the range of from about 350 nm to about 3 micrometer and preferably in the range of about 400 nm to about 1200 nm, Such substance may also consist a layer of black pink, china ink, Indochin green, or any other substance capable of absorbing the radiation in the range. It may also consist of roughing a metallic surface or etching a metallic surface so it traps light and absorbs it, or it may consist of roughing the substrate window 1220 and then painting it or coating it with carbon based absorbing substance, absorbing paint, or any other film or layer of high absorbing substance.

A further elaboration of the present invention, contemplates a third layer, 1227, of high reflective or metallic substance deposited on top of the substance of high absorption layer 1225.

The layer, 1227, place on top of the layer of high absorption 1225 place on top of the window substrate 1220, is layer of substance capable of reflecting the radiating energy from the energy source, 1229 may be placed. Such a substance may consist of a layer of metallic substance. Such a layer of metal substance may, for example, be a layer of aluminum foil, a gold foil, a copper foil, or other metallic layers. Such a layer 1227, may also be deposited by vapor deposition of metal, galvanic methods, painting of metallic or other reflective compound to the window substrate, or other methods, known in the art and familiar to a person with common skill in the art, to allow adherence or contact or attachment of the metallic layer 1227 to the substance of high absorption and to the window substrate material 1220.

Such a layer of metallic material 1227 may serve two purposes, one to reflect any unwanted radiation away from the skin, and two, to even out the distribution of thermal energy across the treatment area.

In further embodiment, a series of opening of a predetermined pattern are made in the layers 1225, and 1227 so that energy from the source, 1229 may be allowed to travel through the window 1220 and the various subsequent layers 1225, 1227 to the target skin to create the desired therapeutic effects, for example, skin rejuvenation and skin healing, treatment of scars and acne scars, and treatment and prevention of active acne.

The sequence of layers between the energy source 1229 and the surface of the skin, 1233 is: a window substrate layer, 1220, a substance of high absorption, 1225, a substance of high reflection or a metallic substance layer 1227, and a the series of holes or opening made through the layers 1227 and 1225 as represented by the holes, 1230, the holes 1230 are holes in every layer 1227, 1225, except for the window substrate 1220.

In a further preferred embodiment, an Opto-thermal coupler for Flash Lamp Acne treatment device is treatment. We abbreviate it with: OTC-IPOT, or: Opto-Thermal Coupler-Intense Pulse Opto Thermal Wand OTC-IPOTW.

In one preferred embodiment, slices of clear plastic windows, for example, polycarbonate material, or high temperature plastic (i.e. a plastic that is capable of withstanding transient temperatures of up to about 1000 degree C. and preferably temperature of up to 370 degree C. or at the very minimum window material plastic capable of withstanding a temperature of at least over 200 Degree C.) may be used as a window material to allow transfer of the energy from the energy source in the enclosure to the targeted material or skin.

Figure 13:
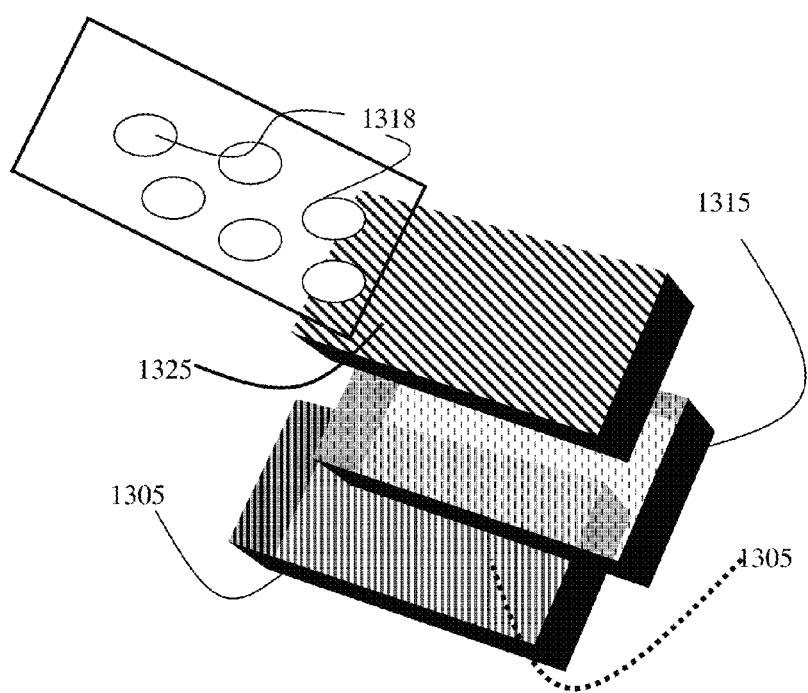
FIG. 13 shows the layer of such opto-thermal converters

FIG. 13 shows some of the features of and layer of such opto-thermal converter window. The window side facing the energy source, 1305 remain clear thus allowing energy and in particular optical or light energy to travel through it. A layer of high absorbing material 1315 is laid on top of the opposite end of the transparent window and a layer of high thermally conducting material such as aluminum foil or metal vapor deposition 1325, is laid upon the layer of high absorbing substance 1315.

The layer of conducting substance 1325 can cover the entire window surface are or just a portion of it the aluminum foil (normal OR heavy duty) machine/sanded and coated with absorbing black, glued to it and would range in thickness from 0.1 micrometer to as much as a mm and preferably from about 3 micrometer to about 200 micrometer. The layer of high absorbing substance 1315 can have similar dimensions except that its thickness can range from about 0.01 micrometer to as much as about 300 micrometer and preferably from 1 micrometer to 50 micrometer.

Optionally a plurality of holes are placed across each and every layer (as a drilled column) 1318 to allow some energy, electromagnetic (EM) energy, light, or other radiating energy, to propagate through the windows and the sequence of layers to the skin or target surface.

Figure 14:
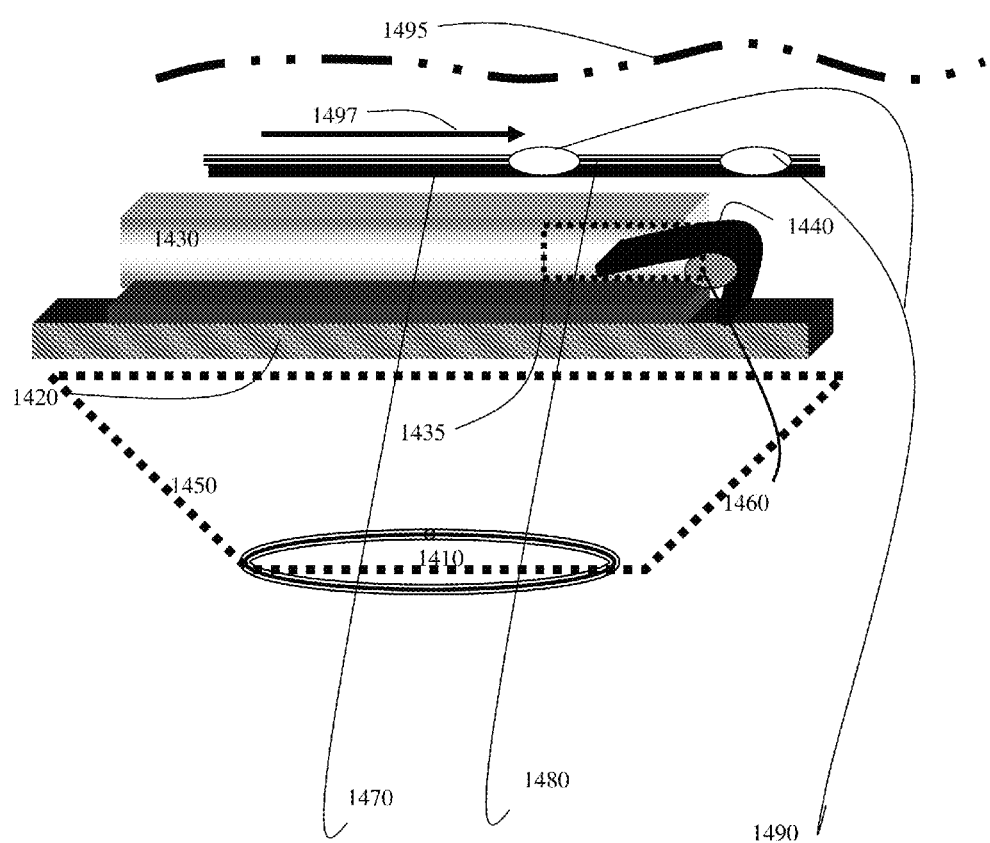
FIG. 14 shows the mounting an opto-thermal converter and its loading of onto a handpiece

FIG. 14 shows another preferred embodiment illustrating a method and apparatus for mounting an opto-thermal converter loading of onto a handpiece or a handheld device designed for converting source energy, preferably light or electromagnetic (EM) energy, into thermal energy for treatment of targeted surface, skin, tissue, and skin ailment treatment and conditioning.

The device includes, as described above, an energy source 1410 contained in the handpiece, the output window 1420, a slide or filter made of glass, plastic, polycarbonate or other material, an source energy-thermal energy converter 1430 whose components are described above in relation to FIG. 13. The Assembly 1430 has a notch in it, 1435 to allow it to be pushed against a clamp, 1440, for example a piece of bent metal anchored on one side to the window 1420 or enclosure 1450, and capable of exerting elastic pressure if its other end is lifted from its deformed position. When the slide or converted assembly 1430 is pushed with its notch 1435 into and under the clamp 1440, is can then be held in place against the window 1420. Further, the an interlock 1460 can be inserted under the clamp 1440 or in other locations, so that when pushed by the edge of the notch 1435 in the converter assembly 1430 activation of the energy source 1410 is possible ONLY if the converter assembly is pushed fully into and under the clamp 1440, so that no energy is allowed to be emitted nor is the energy source 1410 activated unless the converter assembly 1430 is pushed fully in and placed properly over the window 1420.

Optionally a layer of absorbing substance 1470 or substance capable of absorbing the energy of the source 1410, followed by a layer or a coat of conducting material 1480 such as aluminum or copper foil, a layer of conducting metal such as vapor metal deposit is deposited or coated over the layer of substance capable of absorbing the energy source (SCAES), 1470. Optionally the two layers 1470 and 1480 has holes or opening 1490 in them to allow at least some of the sources energy to propagate unperturbed or possibly filtered, into the target material or skin 1495. Finally the arrow, 1497 illustrate the direction of that the opto-thermal converter assembly 1430 should be pushed in order to slide under clamp 1440 and to fully press the interlock 1460 to allow activation of the energy source 1410.

Figure 15:
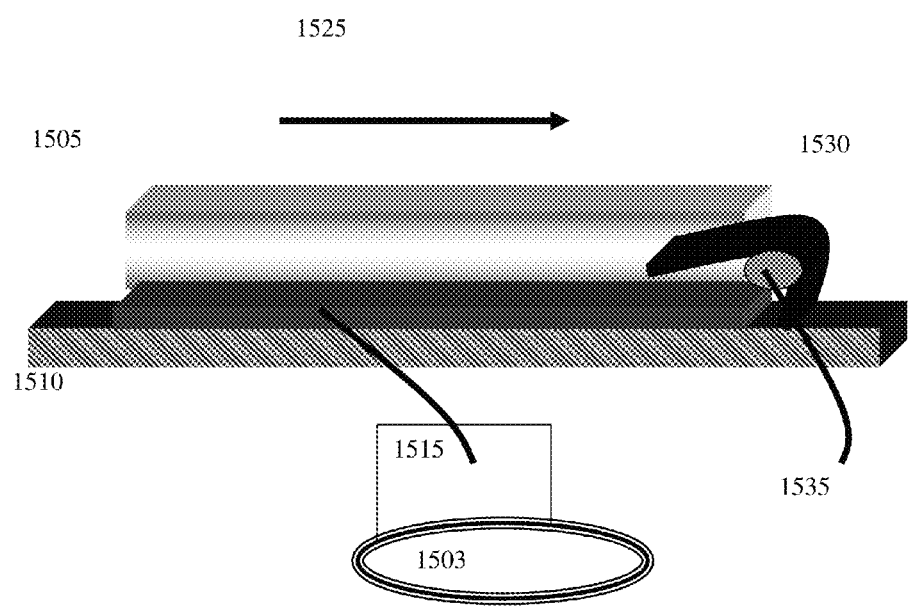
FIG. 15 shows another embodiment illustration of the way an opto-thermal converter or opto-thermal coupler assembly may be assembled and used with a spring-laded holder with an interlock.

FIG. 15 shows another illustration of the way an opto-thermal converter or opto-thermal coupler assembly may be assembled and used with a spring-laded holder or clamp equipped with an interlock. Here, a window 1515 is attached to the frame of the box 1510 to allow energy to come out from the energy source 1503. The optothermal coupler or optothermal converter assembly 1505 is pushed in the direction indicated by the arrow 1525 under a clamp or a holder 1530 which can be made of a spring loaded or a metal clamp with elasticity so it can push down against the lower lip of the Opto-thermal assembly 1505 notch, to hold it down and fixed in place. An interlock 1535, can then be pushed by the lower lip of the optothermal converter assembly to ensure activation of the source ONLY when the optothermal converter assembly is fully in lace and secured against the window. 1515.

Figure 16:
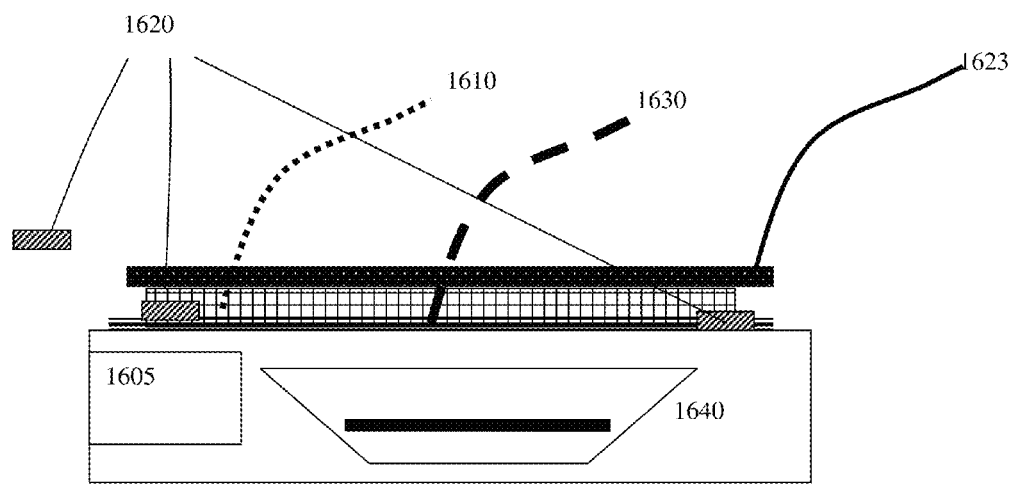
FIG. 16 shows another design of an Opto-thermal coupler to be mounted on top of the output window.

FIG. 16 shows another preferred embodiment for the design Front Opto-thermal coupler to be mounted on top of Window 1630 in the enclosure. As shown in the figure a layer of supporting frame 1610 is attached by means, for example, of a double sided tape or Velcro® hooks and loops, 1620 into the frame 1605 or window 1630. On top of the frame a layer, 1623 of substance capable of absorbing energy or EM radiation is placed to be contacted with the targeted material or skin or tissue to be treated. On top of the layer of high absorbing substance a layer of conducting material can be placed. Optionally holes in the layers of conducting material and high absorbing materials 1623 can be made to allow a pattern of direct energy, EM energy or light from the energy source 1640 to emerge and contact the target material or skin or tissue directly. 1612 shows an alternative support frame for the optothermal converter film 1623, the support frame 1612 has more holes or openings and more support structures and support lines in its frame.

Figure 16B:
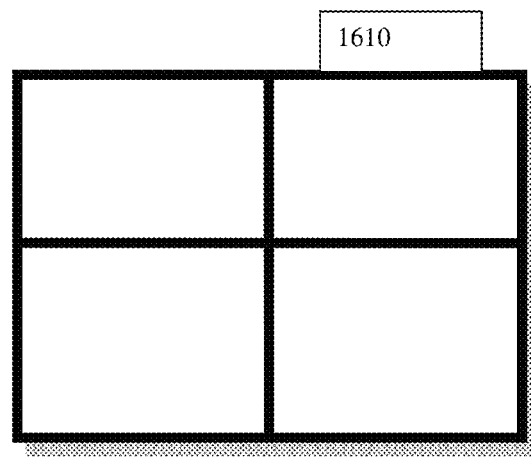
FIG. 16B shows another possible configuration of the frame and layer of high absorbing substance in an optothermal coupler.
Figure 16B:
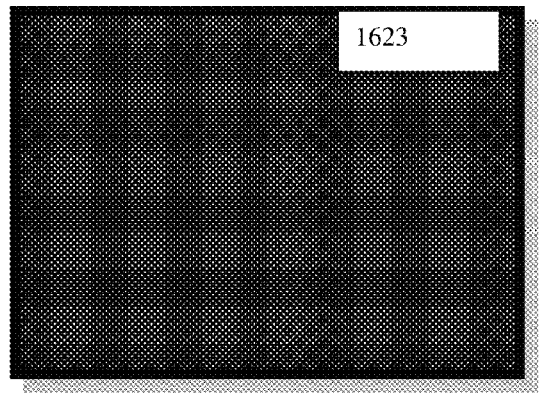
Figure 16B:
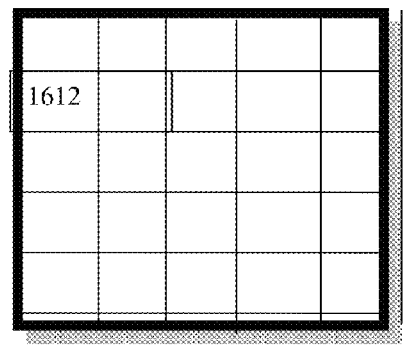
Figure 16B:
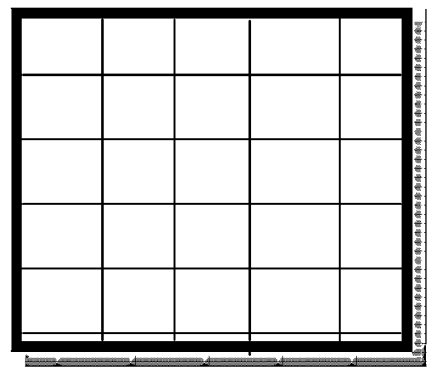

FIG. 16B shows a top view of one possible configuration of the frame 1610 and layer of high absorbing substance 1623. The support frame height can possibly be between about ~0.0001 mm to about 3 cm, and preferably between about 50 micrometer and 1 mm. The film absorbing layer height can be from about 0.1 micrometer to about 2 mm and preferably between about 5 micrometer and 500 micrometer. (where 1 mil is about 25 micrometer).

The high absorbing layer can be placed on a High temperature plastic, paper, tracking paper, a thin film or aluminum covered with ABSORBE, tracing paper. The thin film can be sanded or sand blasted or roughened to allow better adherence. 1612 shows an alternative structure of the support frame that could be used according to the teaching of the present invention.

The use of a high conductive layer on top of the high absorbing layer in the opto-thermal converter assembly often can generate a hotter more energize opto-thermal converter with a more efficient conversation of the source energy into thermal energy. The reason it such a high conducting layer, for example, a layer of metal, or for example a layer of thin aluminum foil or a copper foil, each such foils of thicknesses from about 1 micrometer to about 1 mm an preferably from about 10 micrometer to about 150 micrometer, for example, foils such as those ready available for commercial use in the supermarkets, drug store etc. for example, regular kitchen use aluminum foil or "heavy duty" aluminum foil The apparent better heating of the High Absorbing substance (HAS) coated aluminum foil or other metal foil, may be because if only HAS layer is used, some source energy, or EM energy or light energy may leaks through the HAS layer into the skin, wherein with the metal or good conductor method, it does not. Hence light bounces in the small cavity (between the reflecting material coated reflector over the lamp, and the opto-thermal converter), until fully absorb by the absorbing layer then rapidly conducted to the skin.

Figure 17:
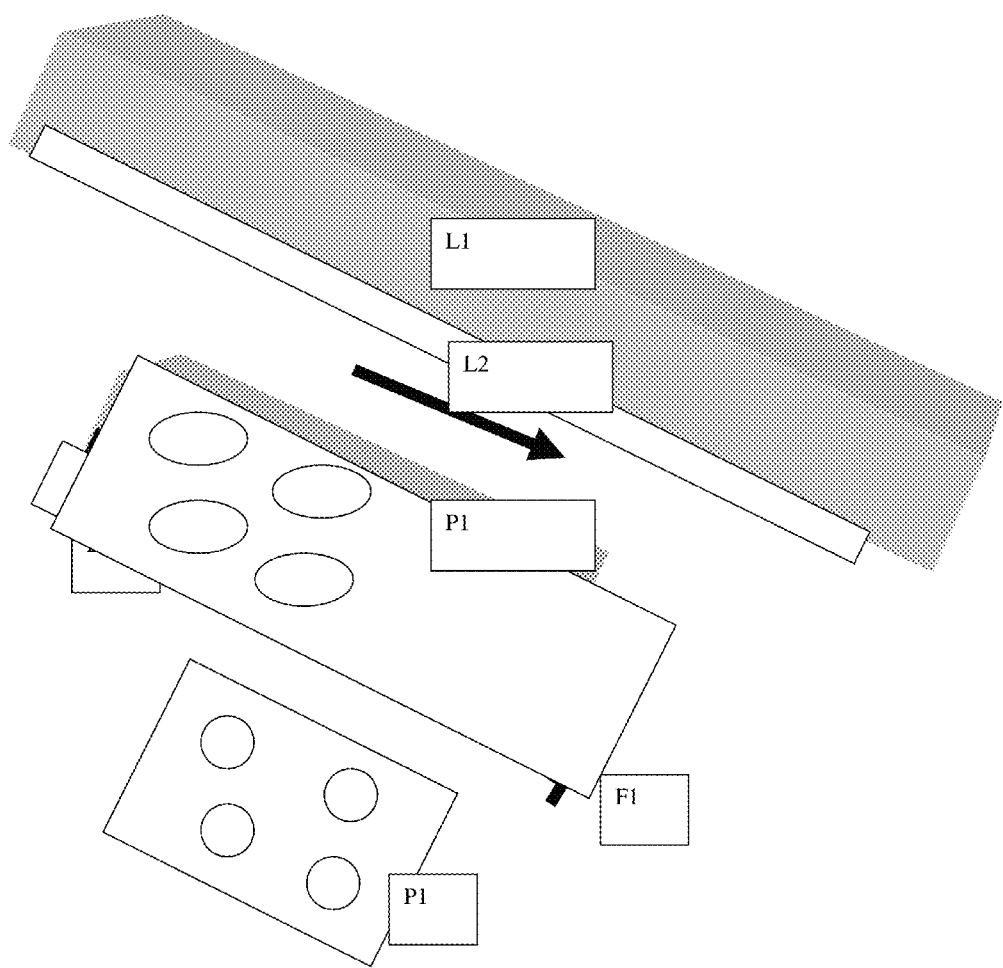
FIG. 17 shows another optothermal coupler utilizing aluminum.

Yet another preferred embodiment is shown in FIG. 17. Here, in this embodiment, the layer L3 is now a transparent window (from about 300 nm to 1400 hm), the HAS coat layer is L2 and a layer L1 is made of Aluminum (or other conducting metal or conducting or insulation material layer L1) is on top L1. The window L3 has a cavity drilled in it where the holder H1 (spring loaded with fastener F1, to fasten to the box surface) can be mounted. The whole assembly slide in the direction of the arrow A1 to be mounted and held by the holder H1.

Alternatively, the layer L3 can be a lamination over the HAS, and over the aluminum metal layer. Alternatively, the Layer L3 can be a thin glass or transmitting plastic. Where the light go through and into the HAS and aluminum. With the interlock/counter you can have NO light while the OTC is not in. AND count how many times it is being put in.

Layer 1 (L1) can be Aluminum, Or a high temp plastic, or any other metal or conducting or insulating material. Layer 2 is high absorbing. P1 shows possible patterns. Configurations: 1) A thin layer of 10-40 um aluminum coated with HAS. This allows rapid and uniform heating—generating a step function of heating=temporal heating profile. 2) A plastic layer with L2 being HAS. This allows slower heating, slower—mellower diffusion profile. 3) With various holes shapes, that is a plurality of holes or perforations of various shapes in the layer of absorbing and reflecting or high conducting materials.

Holes are in aluminum, in HAS layer, in plastic, or a combination thereof.

Figure 18:
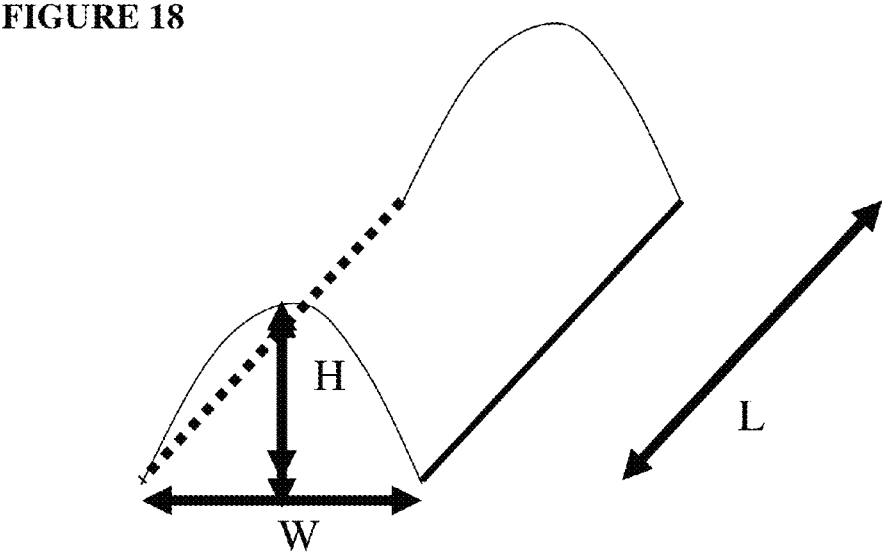
FIG. 18 shows the design of a lamp reflector.
Figure 18:
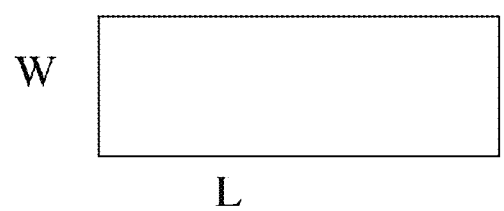

In yet another preferred embodiment shown in FIG. 18 the reflector assembly for an energy source, preferably a flash lamp of the type use in flash photography such as disposable cameras or digital cameras, or possibly with up to about 3 to 10 times as much optical energy as those and preferably with a lamp up to about twice as long but with energy up to 2 to 4 times as much as those in disposable cameras. A simple flash lamp such as those used in disposable camera is used along with a window with metallic coating and high absorbing substance. The window can have the following dimension where, L is of course determine by the length of the window and is of about 0.5 cm to 2 cm and preferably 1.5 cm. The width, W, should be from about 0.2 cm to about 2.5 cm and preferably about 1 cm wide. The height of the reflector, H, (for example an aluminum reflector) can be from about 0.2 cm to about 4 cm and preferably about 1 cm.

Figure 19:
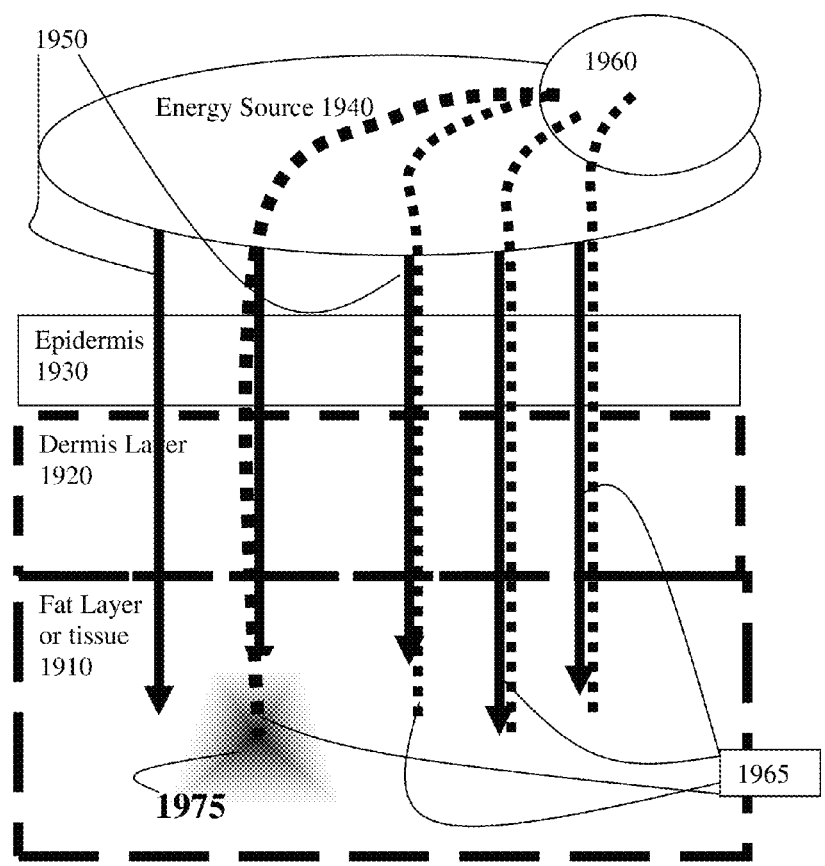
FIG. 19 shows a device and method for reducing body fat.

Yet another preferred embodiment is shown in FIG. 19. Here a method for reducing body fat and minimally invasive skin rejuvenation or face lift, or body shaping is illustrated. The method or device contemplated are as follows. An energy source, preferably a light source, a laser, an RF source or an electric heater source, is delivered into the tissue with small protruding probes. Here an energy source 1940 deliver energy to probes 1950 which intern deliver the energy to the tissue, or skin, or target material, most often to the dermis 1920 or fat layer 1910 below the dermis. In a preferred embodiment of this method, the energy source deliver light or EM energy or laser energy, or visible laser energy. In such a preferred embodiment, the probes, 1950 a hollow and contain optical fiber, for example capable of delivering laser energy. In a further elaboration of a preferred embodiment, such laser energy delivered from the source 1940 through the probes 1950 is of a visible or near IR wavelengths. In this embodiment, the probes or ducts are hollow tubes, for example, syringes and are capable of delivering energy and also a substance of high absorption (HAS) liquid or fluid stored in a container next to the energy source, 1960. The substance of HAS contained in the container 1960 is then delivered to a point in front of the fibers or probes 1950. Preferably, such HAS can also be labeled with fluoresce material or radioactive label or other labeled that can be viewed with imaging systems (imaging systems such as ultrasound, CT, PET, X-rays, cat scan, florescence imaging, OCT=optical coherent topography or variation of OCT, such as polarization sensitive OCT, florescence detection, opto-acoustics detection, IR or thermal imaging or any other imaging system known to those skilled in the art. Deposition of the such HAS fluid or liquid from the reservoir 1960 in the tissue, skin, fat or other target material can then be monitored with the above mentioned, imaging methods or other possible imaging methods known to those skilled in the arts, and the extent of the HAS or high absorbing liquid can be viewed and monitored. For example, spot of HAS 1975 can be created in front of the HAS delivery 1965. The spot can be monitored with the above mentioned imaging system or simply decided upon by the determining how much HAS fluid to deliver though the tube 1965. Subsequent to the delivery of the HAS from the reservoir 1960 to the targeted region, the energy source can be activated and upon being absorbed my the HAS 1975, damage to the targeted stained, or labeled, area can be achieved. For example, a carbon based liquid can be delivered or a PDT type material, or any other absorber can be delivered to the fat layer 1910 and subsequently a dose of light, for example a visible laser light, or incoherent broad band light, or light from superluminescent diode, can be delivered to the tissue are labeled by the HAS through an optical fiber or other energy delivery means such as hollow waveguide, metal tubes, or other light, EM energy or other energy delivery means. A sufficient amount of light energy dosage or energy density, delivered for a sufficient amount of time can achieve irreversible damage or other type of damage to allow removal or denaturation or other effect on the tissue, fat or skin to reduce the amount of fat, achieve controlled coagulation, or other desired biological effect such as fat reduction, skin rejuvenation, selective destruction of cancer tumor or benign tumors or benign growths, or other desired effects. The amount of energy and energy dosage and energy delivered time parameters necessary to achieve such tissue effects has been studied and documented and are well known to those skilled in the art.

Yet another embodiment contemplate the deposition of nano-particles 1975 capable of enhancing absorption in front of the light delivery conduits or optical fiber and then, subsequently, delivering the light dose. For example gold nano-particles are capable of enhancing the absorption of the environment they are deposited in, thus, depositing gold particle in a tissue or fat layer to be targeted for destruction, or to be changed sufficiently so that it can be removed by artificial or natural means, or by the body own mechanism of removing denatured or altered tissue. Thus the nano-particles can be imaged to pinpoint the location and extent of the targeted volume prior to activation of the source energy or light, and then possibly utilized to create specially localized absorption in the target tissue by the dose of light launched from the optical conduits or optical fibers.

In a similar way, a method for treating wrinkles is also contemplated by the present invention. In a preferred embodiment, the device and method described by FIG. 19 are used to create selective damage to muscle tissue responsible for wrinkles caused by muscular activity such as frown lines. In this embodiment, the method described above in connection with FIG. 19 is used to cause temporarily or permanent damage or paralysis to the muscle responsible for the wrinkles, frown line, thus resolving the frown line or wrinkles or other deformation of the skin or tissue. In this case, the method works substantially in the same as described above for destruction or reduction of fat layers or tissue, except that in this case, the layer 1910 represent a muscle tissue to be temporarily destroyed or paralyzed or permanently destroyed or paralyzed.

Figure 20:
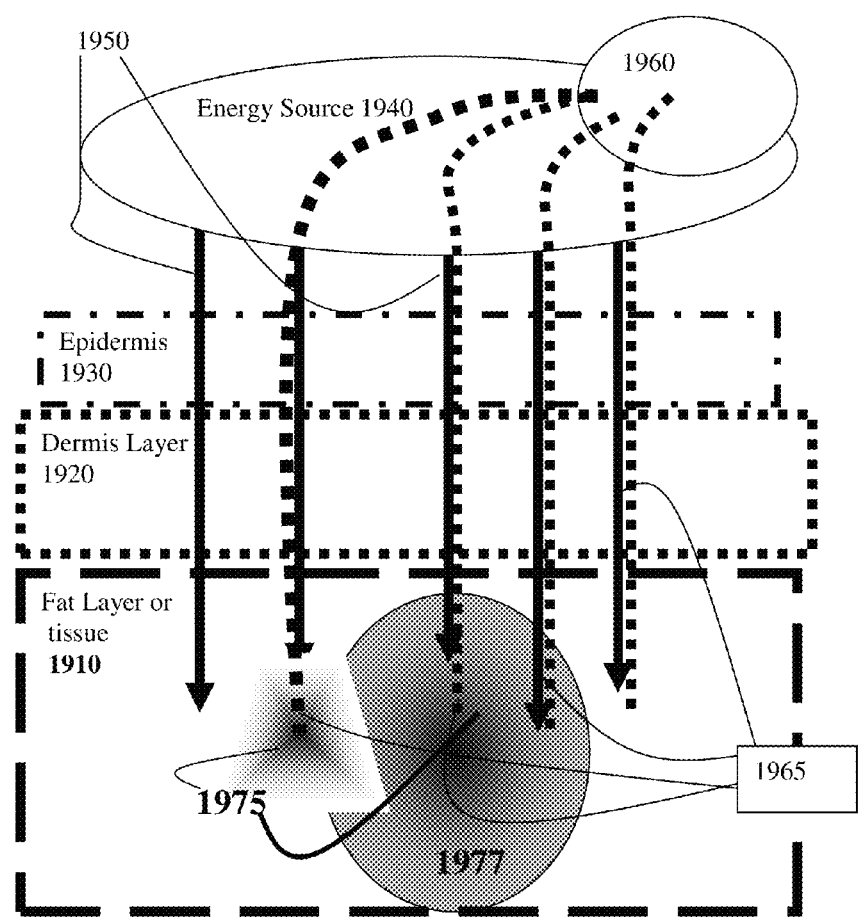
FIG. 20 shows illustration of how a body fat reducing method and device may be designed.

FIG. 20 shows the diffusion of light emanating (a scatter "ball" of photons diffusing propagating through the tissue) or exiting from the optical fiber or conduit 1950 and propagating through the tissue. If the wavelength of the light is not naturally substantially well absorbed by the tissue, the absorbing enhancing substance 1975 may be used to enhance absorption and define (by the extent of the occurrence of the absorbing enhancing substance) the spatial extent of the interaction.

In a preferred embodiment the invention contemplates several windows.

For examples, windows with thicknesses as listed below may be used:

1) a window with thickness of 1-4 mil=25 to 100 um. The window may have the High Absorbing Substance (HAS) on the window side facing the skin. The window may have with HAS applied to an aluminum layer which is glued or attached to a glass layer or a glass window such as a cover slip where in the glass is facing the light or energy source, and the aluminum is in contact with the skin 2) With a Glass slide where the Aluminum is with larger thermal mass. Need to image thermal with 2 to 5 layers Semi infinite medium.

3) A window made of aluminum with holes patterned into the aluminum layer

4) A window or treatment tip made of aluminum with an absorber pattern painted or applied to certain spots on the side of the aluminum window or treatment tip facing the energy source or light source. Various contemplated advantages include: efficacy for treating acne and skin conditions; safety while treating acne and skin condition and preventing acne; and how the method and device work.

The device itself may comprise among other things, a Hand Held Home Use Hair treatment device.

A low power flash lamp 100 is powered by a battery 110 or a power plug 120 which charges a capacitor 130. The lamp 100 is willfully triggered and controlled through the use of a control board 140 and an activator switch 150.

The lamp 100 (or any other energy source) is housed in the consol 10 and its operation is also controlled by plurality of guards 30. the protruding guards are protruding out of side of the device 10 facing the skin or the human body. The guards 30 are connected to the control of the lamps and do not allow the lamp to fire unless they are ALL depressed to at least a certain depth. For example the depth is such that most of the light from the lamp 100 can not escape sideways and is only directed forward towards the skin. The energy source 100 can be laser or light source, flash lamps, LED, RF, Microwave, any kind of Electromagnetic (EM) energy source, any kind of radiative EM, energy source, thermal energy source, or thermal cooling source (negative or out of the target area flow of energy) energy source.

Only when all protruding guards 30 are full depressed can the flash lamp fire. This arrangement prevents accidental firing of the lamp into the eye.

The Protruding guards 30 can be made of transparent material such as, for example, plastic or glass. The idea is that a protruding guards (PI) array 30 will ensure that the eye is closed PRIOR and BEFORE firing of the lamp.

FIG. 2 shows the same device as in FIG. 1 except that the protruding guards (PG) 30 are made of transparent material to minimize intercept of energy. The PG 30 may also be made of substance capable of cooling the surface with which it is in contact so allow protection of the epidermis, further energy control, energy removal from the target tissue or surface being treated.

FIG. 3 shows the same apparatus as in FIG. 1 except that instead of a plurality of protruding guards PG only one is being used, 30. the protruding guard can have all kind of desired properties: It may be made of cooling (active or passive cooling) so as it is pressed against the skin it also cools. It may be made of transparent material to allow more energy to get into the skin. It may be made of substance or mechanism capable of heating or energizing the skin or delivery energy into the skin. It may be made of absorbing material so that as it is being pressed against the skin it also absorbs energy generated by a light or lasers or any other EM Radiative energy source to absorb the energy and conduct it further into the treated surface or targeted surface.

A predetermined "press Level" i.e. the amount of physical depression in of the protruding guards PG in the direction of the arrow, can be determined and built into the device. FIG. 3 also shows such a pre-determined depression of the PG, 301, before they allow activation of the device. Such a displacement in the PG extension out of the treatment head surface 305 can be built into the device to prevent firing before the device is brought to such predetermined proximity to the surface of the target area. The PG can also have a maximum "collapse distance" or press-distance where the PG can then prevent a contact CLOSER than the predetermined level.

The above descriptions and illustrations are only by way of example and are not to be taken as limiting the invention in any manner. One skilled in the art can substitute known equivalents for the structures and means described. The full scope and definition of the invention, therefore, is set forth in the following claims.

I claim:

1. A method for treating tissue, the method comprising:
    directing an energy output of an energy emitter towards a tissue;
    engaging a plurality of movable members with the tissue, each of the plurality of movable members disposed at least partially in a path of the energy output between the energy emitter and the tissue, and wherein at least some of the energy output is emitted through the plurality of moveable members; and
    emitting the energy output of the energy emitter in response to movement of at least one of the plurality of movable members in the path of the energy output, wherein at least some of the energy output is emitted through the plurality of moveable members.

2. The method of claim 1, wherein the step of emitting the energy output further comprises always maintaining the plurality of movable members in the path of the energy output between the energy emitter and the tissue during energy output of the energy emitter.

3. The method of claim 1, wherein the step of emitting the energy output further comprises emitting a first energy sufficient to cause damage to a retina of an eye.

4. The method of claim 1, further comprising precluding the energy emitter from emitting the energy output unless at least two of the plurality of movable members are depressed by a physical force sufficient to cause discomfort to injury prone tissue locations.

5. The method of claim 1, further comprising emitting an aiming beam from the energy emitter, the aiming beam having a lower energy density than the energy output.

6. The method of claim 1, further comprising emitting an aiming beam from the energy emitter, the aiming beam having a different wavelength than the energy output.

7. The method of claim 1, further comprising configuring at least two of the plurality of movable members such that the at least two movable members are coupled to a common foot.

8. The method of claim 1, further comprising absorbing at least 30% of the energy output with an expanded portion of at least one of the plurality of movable members.

9. The method of claim 1, further comprising actively cooling the plurality of movable members with a cooling element after the energy output.

10. The method of claim 9, further comprising maintaining an epidermal-dermal junction below 50° C. with the cooling element when the energy output is applied at an energy density of at least 1 J/cm$^2$ to the tissue, the tissue having the epidermal-dermal junction.

11. The method of claim 9, further comprising activating the cooling element at a predetermined time subsequent to a detected movement of at least one of the plurality of movable members.

12. The method of claim 1, further comprising dispensing a fluid through a fluid path coupled to at least one of the plurality of movable members.

13. The method of claim 1, further comprising heating at least a portion of the tissue with a resistive heating element coupled to at least one of the plurality of movable members.

14. The method of claim 1, further comprising preventing direct contact between the energy emitter and the tissue.

15. The method of claim 1, further comprising precluding the energy emitter from emitting the energy output unless the plurality of movable members are depressed by a force sufficient to reduce blood circulation in the tissue above a mid-reticular dermis of the tissue.

16. A method for treating tissue, the method comprising:
    directing an energy output of an energy emitter towards a tissue;
    engaging a plurality of movable members with the tissue, wherein each of the plurality of movable members extends from a tissue adjacent face of the energy emitter and each of the plurality of movable members is always disposed in a path of the energy output between the energy emitter and the tissue, wherein the plurality of movable members do not allow the energy emitter to emit the energy output unless at least one of the plurality of movable members is depressed by the tissue a predetermined distance with sufficient force to cause discomfort to injury prone tissue locations, wherein the predetermined distance is less than 5 mm; and emitting the energy output of the energy emitter in response to movement of the at least one of the plurality of movable members relative to the energy emitter, wherein at least some of the energy output is emitted through the plurality of moveable members.

17. A method for treating tissue, the method comprising:

Aiming an energy generating source at a target tissue area;

Bringing the energy generating source to the vicinity of the target tissue area;

Engaging at least two probe members with the target tissue area, wherein the at least two probe members extend from a tissue adjacent face of the energy generating source and the at least two probe members are each disposed between the energy generating source and the target tissue area;

Generating a feedback signal to the energy generating source based on the engagement of the probe members with the target tissue area; and Emitting an energy from the energy generating source directed to the target tissue area in response to the feedback signal, wherein at least some of the energy output is emitted through the plurality of moveable members.

* * * * *